(12) United States Patent
Xu et al.

(10) Patent No.: US 8,319,011 B2
(45) Date of Patent: Nov. 27, 2012

(54) TOBACCO PLANTS HAVING REDUCED NICOTINE DEMETHYLASE ACTIVITY

(75) Inventors: Dongmei Xu, Glen Allen, VA (US); Mark T. Nielsen, Nicholasville, KY (US); Yanxin Shen, Glen Allen, VA (US)

(73) Assignee: U.S. Smokeless Tobacco Company LLC, Richmond, VA (US)

( * ) Notice: Subject to any disclaimer, the term of this patent is extended or adjusted under 35 U.S.C. 154(b) by 491 days.

(21) Appl. No.: 12/484,975

(22) Filed: Jun. 15, 2009

(65) Prior Publication Data

US 2010/0012137 A1 Jan. 21, 2010

Related U.S. Application Data

(63) Continuation-in-part of application No. PCT/US2007/087386, filed on Dec. 13, 2007.

(60) Provisional application No. 61/098,601, filed on Sep. 19, 2008.

(51) Int. Cl.
*A24B 13/00* (2006.01)
*A24D 1/00* (2006.01)
*A01H 1/00* (2006.01)
*A01H 5/00* (2006.01)
*A01H 5/10* (2006.01)

(52) U.S. Cl. ............ 800/270; 800/317.3; 131/271; 131/352; 131/360; 131/366

(58) Field of Classification Search .......... 800/266, 800/270, 317.3
See application file for complete search history.

(56) References Cited

U.S. PATENT DOCUMENTS

| | | |
|---|---|---|
| 4,693,976 A | 9/1987 | Schilperoort et al. |
| 4,732,856 A | 3/1988 | Federoff |
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,322 A | 7/1991 | Rogers et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,302,523 A | 4/1994 | Coffee et al. |
| 5,352,605 A | 10/1994 | Fraley et al. |
| 5,378,619 A | 1/1995 | Rogers |
| 5,384,253 A | 1/1995 | Krzyzek et al. |
| 5,463,174 A | 10/1995 | Moloney et al. |
| 5,464,763 A | 11/1995 | Schilperoort et al. |
| 5,464,765 A | 11/1995 | Coffee et al. |
| 5,469,976 A | 11/1995 | Burchell |
| 5,472,869 A | 12/1995 | Krzyzek et al. |
| 5,583,021 A | 12/1996 | Dougherty et al. |
| 5,595,733 A | 1/1997 | Carswell et al. |
| 5,614,399 A | 3/1997 | Quail et al. |
| 5,641,664 A | 6/1997 | D'Halluin et al. |
| 5,679,558 A | 10/1997 | Gobel et al. |
| 5,712,135 A | 1/1998 | D'Halluin et al. |
| 5,766,900 A | 6/1998 | Shillito et al. |
| 5,929,304 A | 7/1999 | Radin et al. |
| 6,002,070 A | 12/1999 | D'Halluin et al. |
| 6,074,877 A | 6/2000 | D'Halluin et al. |
| 6,907,887 B2 | 6/2005 | Conkling |
| 6,953,040 B2 | 10/2005 | Atchley et al. |
| 7,032,601 B2 | 4/2006 | Atchley et al. |
| 7,884,263 B2 * | 2/2011 | Dewey et al. ......... 800/285 |
| 2002/0042934 A1 | 4/2002 | Staub et al. |
| 2004/0035745 A1 | 2/2004 | Jackson |
| 2004/0103449 A1 | 5/2004 | Xu |
| 2004/0111759 A1 | 6/2004 | Xu |
| 2004/0117869 A1 | 6/2004 | Xu |
| 2004/0162420 A1 | 8/2004 | Xu |
| 2005/0132444 A1 | 6/2005 | Xu |
| 2005/0160493 A9 | 7/2005 | Ratcliffe et al. |
| 2005/0178398 A1 | 8/2005 | Breslin et al. |
| 2005/0223442 A1 | 10/2005 | Xu |
| 2005/0244521 A1 | 11/2005 | Strickland et al. |
| 2006/0037096 A1 | 2/2006 | Xu |
| 2006/0037623 A1 | 2/2006 | Lawrence |
| 2006/0041949 A1 | 2/2006 | Xu et al. |
| 2006/0185686 A1 | 8/2006 | Lawrence |
| 2006/0191548 A1 | 8/2006 | Strickland et al. |
| 2007/0149408 A1 | 6/2007 | Thomas et al. |
| 2007/0199097 A1 | 8/2007 | Xu et al. |
| 2007/0292871 A1 | 12/2007 | Xu |

FOREIGN PATENT DOCUMENTS

| | | |
|---|---|---|
| EP | 0 267 159 | 5/1988 |
| EP | 0 159 418 | 5/1990 |
| EP | 0 176 112 | 5/1990 |
| EP | 0 120 516 | 10/1991 |
| EP | 0 131 624 | 9/1992 |

(Continued)

OTHER PUBLICATIONS

Gavilano, L. et al. The Journal of Biological Chemistry, Jan. 5, 2007; (Published Nov. 13, 2006 in JBC Papers in Press) vol. 282, No. 1; pp. 249-256.*

(Continued)

*Primary Examiner* — Russell Kallis
(74) *Attorney, Agent, or Firm* — Fish & Richardson P.C.

(57) ABSTRACT

The present invention generally relates to methods and materials involved in producing tobacco plants having reduced levels of conversion of nicotine to nornicotine. In certain embodiments, the invention is directed to mutations in a nicotine demethylase gene, tobacco plants comprising mutations in a nicotine demethylase gene, and tobacco compositions and products thereof. In other embodiments, the invention is directed toward nicotine demethylase RNA interference, tobacco plants comprising a nicotine demethylase RNA interference transgene, and tobacco compositions and products thereof.

18 Claims, 9 Drawing Sheets

FOREIGN PATENT DOCUMENTS

| | | |
|---|---|---|
| EP | 0 292 435 | 7/1995 |
| EP | 0 116 718 | 5/1996 |
| EP | 0 627 752 | 7/1997 |
| EP | 1 033 405 A2 | 9/2000 |
| EP | 0 290 799 B9 | 9/2004 |
| EP | 0 320 500 | 11/2004 |
| WO | WO 87/06614 | 11/1987 |
| WO | WO 92/09696 | 6/1992 |
| WO | WO 93/21335 | 10/1993 |
| WO | WO 94/01930 | 1/1994 |
| WO | WO 02/072758 | 9/2002 |
| WO | WO 03/078577 | 9/2003 |
| WO | WO 2004/035745 | 4/2004 |
| WO | WO 2005/038018 | 4/2005 |
| WO | WO 2005/038033 | 4/2005 |
| WO | WO2005/046363 | 5/2005 |
| WO | WO 2005/111217 | 11/2005 |
| WO | WO 2005/116199 | 12/2005 |
| WO | WO 2006/022784 | 3/2006 |
| WO | WO 2006/091194 | 8/2006 |
| WO | WO 2006/120570 | 11/2006 |
| WO | WO 2008/076802 | 6/2008 |

OTHER PUBLICATIONS

U.S. Appl. No. 11/694,507, filed Mar. 30, 2007, Xu.
U.S. Appl. No. 60/337,684, filed Nov. 13, 2001, Xu.
U.S. Appl. No. 60/347,444, filed Nov. 11, 2002, Xu.
U.S. Appl. No. 60/363,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 18, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/665,451, filed Mar. 24, 2005, Xu.
Adams et al., "Genes duplicated by polyploidy show unequal contributions to the transcriptome and organ-specific reciprocal silencing," *Proc Natl Acad Sci USA*, 2003, 100(8):4649-4654.
Allen et al., "RNAi-mediated replacement of morphine with the nonnarcotic alkaloid reticuline in opium poppy," *Nature Biotechnology*, 2004, 22:1559-1566.
Alonso et al., "A *Hox* gene mutation that triggers nonsense-mediated RNA decay and affects alternative splicing during *Drosophila* development" *Nucleic Acids Research*, 31(14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt and Rank, "Colocalization of antisense RNAs and ribozymes with their target mRNAs," *Genome*, 1997, 40:785-797.
ARS-GRIN (PI 551280, http://www.ars-grin.gov/cgi-bin/npgs/acc/display.pl?1446216, accessed Feb. 2009) 2 pages.
Asamizu et al., "A large scale analysis of cDNA in *Arabidopsis thaliana*: Generation of 12,028 non-redundant expressed sequence tags from normalized and size-selected cDNA libraries," *DNA Research*, Jan. 2000, 7:175-180.
Bak et al., "Transgenic tobacco and Arabidopsis plants expressing the two multifunctional sorghum cytochrome P450 enzymes, CYP79A1 and CYP71E1, are cyanogenic and accumulate metabolites derived from intermediates in Dhurrin biosynthesis," *Plant Physiol.*, 2000, 123:1437-1448.
Bartoszewski et al., "Cloning of a Wound Inducible *Lycopersicon esculentum* Cytochrome P450 Gene and Lack of Regeneration of Transgenic Plants with Sense or Antisense Constructs," *J. Am. Soc. Hort. Sci.*, 2002, 127(4):535-539.
Baseggio et al., "Size and genomic location of the pMGA multigene family of *Mycoplasma gallisepticum*," *Microbiology*, 1996, 142:1429-1435.
Batard et al., "Increasing expression of P450 and P450-reductase proteins from monocots in heterologous systems," *Archives of Biochemistry and Biophysics*, 2000, 379:161-169.
Baulcombe, "Fast forward genetics based on virus-induced gene silencing," *Curr. Opin. Plant Biol.*, 1999, 2:109-113.
Bolitho et al., "Antisense apple ACC-oxidase RNA reduces ethylene production in transgenic tomato fruit," (1997) *Plant Science* 122: 91-99.
Bosher et al., "RNA interference: genetic wand and genetic watchdog," *Nat. Cell Biol.*, 2000, 2:E31-36.
Bosl and Li, "The role of noise and positive feedback in the onset of autosomal dominant diseases," *BMC Syst Biol*, 2010, 4:93.
Branch, "A good antisense molecule is hard to find," *TIBS*, 1998, 23:45-50.
Brigneti et al., "Viral pathogenicity determinants are suppressors of transgene silencing in *Nicotiana benthamiana*," *EMBO J.*, 1998, 17(22):6739-6746.
Burns et al., "Large-scale analysis of gene expression, protein localization, and gene disruption in *Saccharomyces cerevisiae*," *Genes Dev.*, 1994, 8:1087-1105.
Burton et al., Changes in Chemical Composition of Burley Tobacco During Senescence and Curing. 2. Acylated Pyridine Alkaloids, *J. Agric. Food Chem.*, 1988, 38(3):579-583.
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 1992, 40:1050-1055.
Byers et al., "Killing the messenger: new insights into nonsense-mediated mRNA decay" *The Jounral of Clinical Investigation*, 109(1):3-6 (2002).
Byzova et al., "Transforming petals into sepaloid organs in Arabidopsis and oilseed rape: implementation of the hairpin RNA-mediated gene silencing technology in an organ-specific manner," *Planta* 218:379-387 (2004).
Carron et al., "Genetic modification of condensed tannin biosynthesis in *Lotus corniculatus* .1. Heterologous antisense dihydroflavonol reductase down-regulates tannin accumulation in "hairy root" cultures," *Theoretical and Applied Genetics* 87(8): 1006-1015.
Caruthers, "New Methods for Chemically Synthesizing Deoxyoligonucleotides," *Methods of DNA and RNA Sequencing*, 1983, Chapter 1, Weissman (ed.), Praeger Publishers, New York.
Chai et al., "Reducing the maize amylopectin content through RNA interference manipulation," *Zhi Wu Sheng Li Yu Fen Zi Sheng Wu Xue Buo* 31:625-630 (2005), Abstract Only.
Chakrabarti et al., "CYP82E4-mediated nicotine to nornicotine conversion in tobacco is regulated by a senescence-specific signaling pathway," *Plant Mol. Biol.*, 2008, 66:415-427.
Chakrabarti et al., "Inactivation of the cytochrome P450 gene *CYP82E2* by degenerative mutations was a key event in the evolution of the alkaloid profile of modern tobacco," *New Phytologist*, 2007, 175:565-574.
Chang et al., "Predicting and Testing Physical Locations of Genetically Mapped Loci on Tomato Pachytene Chromosome," *Genetics*, 2007, 176:2131-2138.
Chao et al., "A silent mutation induces exon skipping in the phenylalanine hydroxylase gene in phenylketonuria," *Hum. Genet.*, 2001, 108(1):14-19.
Chappell, "Biochemistry and Molecular Biology of the Isoprenoid Biosynthetic Pathway in Plants," *Annu. Rev. Plant Physiol. Plant Mol. Biol.*, 1995, 46:521-547.
Chapple et al., "Molecular-Genetic Analysis of Plant Cytochrome P450-Dependent Monooxygenases," *Annu. Rev. Plant Physiol. Plant. Mol. Biol.*, 1998, 49:311-343.
Chelvarajan et al., "Study of Nicotine Demethylation in *Nicotiana otophora*," *J. Agroc. Food Chem.*, 1993, 41:858-862.
Cheung et al., "A floral transmitting tissue-specific glycoprotein attracts pollen tubes and stimulates their growth," *Cell*, 1995, 82:383-393.
Cho et al., "Transcriptome Analysis and Physical Mapping of Barley Genes in Wheat-Barley Chromosome Addition Lines," *Genetics*, 2006, 172:1277-1285.
Chou et al., "Chromosome Rearrangements in *Arabidopsis thaliana* Generated Through Cre-*lox* Site Specific Recombination," *Plant and Animal Genome VII Conference Abstracts*, San Diego, Calif., Jan. 17-21, 1999. Abstract No. P133.
Chuang and Meyerowitz, "Specific and heritable genetic interference by double-stranded RNA in *Arabidopsis thaliana*," *Proc. Natl. Acad. Sci. USA*, 2000, 97(9):4985-4990.

Cogoni and Macino, "Post-transcriptional gene silencing across kingdoms," *Genes Dev.*, 2000, 10:638-643.

Colbert et al., "High-throughput screening for induced point mutations" *Plant Physiology*, 126:480-484, (2001).

Collier et al., "A Method for Specific Amplification and PCR Sequencing of Individual Members of Multigene Families: Application to the Study of Steroid 21-Hydroxylase Deficiency," *PCR Meth Appl*, 1992, 1:181-186.

Colliver et al., "Differential modification of flavonoid and isoflavonoid biosynthesis with an antisense chalcone synthase construct in transgenic *Lotus corniculatus*," *Plant Mol. Biol.*, 1997, 35(4):509-522.

Crookshanks et al., 28.8% identical, found in the EST Database. Accession No. BF153877 from The Potato tuber transcriptome: analysis of 6077 expressed sequence tags, *FEBS Lett.*, 2001, 506(2):123-126.

D'Souza et al., "Missense and silent tau gene mutations cause frontotemporal dementia with parkinsonism-chromosome 17 type, by affecting multiple alternative RNA splicing regulatory elements" *Proc. Natl. Acad. Sci. USA*, 96:5598-5603 (1999).

Davuluri et al., "Fruit-specific RNAi-mediated suppression of DET1 enhances carotenoid and flavonoid content in tomatoes," *Nat. Biotechnol.* 23:890-895 (2005).

Dewey et al., Meeting Abstract dated Sep. 27, 2005, 1 page.

Dewey et al., Power point presentation "Functional characterization of the nicotine *N*-Demethylase gene of tobacco" *Philip Morris USA*, 21 pages, 2006.

Donato et al., "Fluorescence-Based Assays for Screening Nine Cytochrome P450 (P450) Activities in Intact Cells Expressing Individual Human P450 Enzymes," *Drug Metab. Dispos.*, 2004, 32(7):699-706.

Einset, "Differential expression of antisense in regenerated tobacco plants transformed with an antisense version of a tomato ACC oxidase gene," *Plant Cell Tissue and Organ Culture* 46(2): 137-141.

Elkind et al., "Abnormal plant development and down-regulation of phenylpropanoid biosynthesis in transgenic tobacco containing a heterologous phenylalanine ammonia-lyase gene," (1990). *Proc Natl Acad Sci U S A* 87(22): 9057-9061.

Escobar et al., "RNAi-mediated oncogene silencing confers resistance to crown gall tumorigenesis," *Proc. Natl. Acad. Sci.* USA 98: 13437-13442 (2001).

Falcón-Pérez et al., "Functional Domain Analysis of the Yeast ABC Transporter Ycf1p by Site-directed Mutagenesis," *J. Biol. Chem.*, 1999, 274(33):23584-23590.

Fannin et al., "Nicotine Demethylation in *Nicotiana*," *Med. Sct. Res.*, 1992, 20:867-868.

Faske et al., "Transgenic Tobacco Plants Expressing Pea Chloroplast Nmdh cDNA in Sense and Antisense Orientation," (1997) *Plant Physiol* 115(2): 705-715.

Fedoroff et al., "Cloning of the *bronze* locus in maize by a simple and generalizable procedure using the transposable controlling element *Activator* (Ac)," *Proc. Natl. Acad. Sci. USA*, 1984, 81:3825-3829.

Fire et al., "Potent and specific genetic interference by double-stranded RNA in *Caenorhabditis elegans*," *Nature*, 1998, 391:806-811.

Force et al., "Preservation of Duplicate Genes by Complementary, Degenerative Mutations," *Genetics*, 1999, 151:1531-1545.

Forsthoefel et al., "T-DNA insertion mutagenesis in *Arabidopsis* : prospects and perspectives," *Aust. J. Plant Physiol.*, 1992, 19:353-366.

Frank et al., "Cloning of Wound-Induced Cytochrome P450 Monooxygenases Expressed in Pea," *Plant Physiol.*, 1996, 110:1035-1046.

Freeman et al., "Quantitative RT-PCR: 124-125 pitfalls and potential," *Biotechniques*, 1999, 26:112-122 and 124-125.

Gavilano and Siminszky, "Isolation and Characterization of the Cytochrome P450 Gene *CYP82E5v2* that Mediates Nicotine to Nornicotine Conversion in the Green Leaves of Tobacco," *Plant Cell Physiol.*, 2007, 48(11):1567-1574.

Gavilano et al. "Genetic engineering of *Nicotiana tabacum* for reduced nornicotine content" *Journal of Agricultural and Food Chemistry*, 54:9071-9078 (2006).

Gavilano et al., "Functional Analysis of Nicotine Demethylase Genes Reveals Insights into the Evolution of Modern Tobacco," *The Journal of Biological Chemistry*, 2007, 282(1):249-256.

Ghosh, "Polyamines and plant alkaloids," *Indian J. Exp. Biol.*, 2000, 38:1086-1091.

Graham-Lorence and Peterson, "P450s: structural similarities and functional differences," *FASEB J.*, 1996, 10:206-214.

Guo et al., "Protein Tolerance to Random Amino Acid Change," *Proc. Natl. Acad. Sci. USA*, 2004, 101(25):9205-9210.

Hao and Yeoman, "Evidence in Favour of an Oxidative N-Demethylation of Nicotine to Nornicotine in Tobacco Cell Cultures," *Journal Plant Physiology*, 1998, 152:420-426.

Hao and Yeoman, "Mechanism of Nicotine *N*-Demethylation in Tobacco Cell Suspension Cultures," *Phytochemistry*, 1995, 477-482.

Hao and Yeoman, "Nicotine N-Demethylase in Cell-Free Preparations from Tobacco Cell Cultures," *Phytochemistry*, 1996, 42(2):325-329.

Hao et al., "Mechanism of Nicotine N-Demethylation in Tobacco Cell Suspension Cultures," Institute of Cell and Molecular Biology, the University of Edinburgh, 1995.

Haseloff and Gerlach, "Simple RNA enzymes with new and highly specific endoribonuclease activities," *Nature*, 1988, 334:585-591.

Helene et al., "Control of gene expression by triple helix-forming oligonucleotides. The antigene strategy," *Ann. N.Y. Acad. Sci.*, 1992, 660:27-36.

Helene, "The anti-gene strategy: control of gene expression by triplex-forming-oligonucleotides," *Anticancer Drug Des.*, 1991, 6:569-584.

Helliwell et al., Funct. *Plant Biol.* 2002, 29:1217-1225.

Henikoff and Comai, "Single-Nucleotide Mutations for Plant Functional Genomics," *Annu. Rev. Plant Biol.*, 2003, 54:375-401.

Herbik et al., "Isolation, characterization and cDNA cloning of nicotianamine synthase from barley," (1999) *Eur J Biochem* 265(1): 231-239.

Hibino et al., "Increase of Cinnamaldehyde Groups in Lignin of Transgenic Tobacco Plants Carrying an Antisense Gene for Cinnamyl Alcohol Dehydrogenase," (1995) *Biosci. Biotec. Biochem* 59:929-931.

Hildering and Verkerk, *The use of induced mutations in plant breeding*, 1965, Pergamon press, pp. 317-320.

Hill and Preiss, "Functional analysis of conserved histidines in ADP-glucose pyrophosphorylase from *Escherichia coli*," *Biochem. Biophys. Res. Commun.*, 1998, 244:573-577.

Hoekema et al., "A binary plant vector strategy based on separation of the Vir- and T-region of the *Agrobacterium tumefaciens* Ti plasmid," *Nature*, 1983, 303:107-118.

Huang et al., "Insights into Regulation and Function of the Major Stress-Induced hsp70 Molecular Chaperone In Vivo: Analysis of Mice with Targeted Gene Disruption of the $hsp70.1$ or $hsp70.3$ Gene," *Mol Cell Biol*, 2001, 21(24):8575-8591.

Ingelbrecht et al., "Posttranscriptional silencing of reporter transgenes in tobacco correlates with DNA methylation," *Proc. Natl. Acad. Sci. USA*, 1994, 91:10502-10506.

Isshiki et al., "Nonsense-mediated decay of mutant waxy mRNA in rice" *Plant Physiology*, 125:1388-1395 (2001).

Jack et al., "Relative stability of nicotine to nornicotine conversion in three burley cultivars," *Coresta Congress*, 2004, Kyoto, Agro-Phyto groups, Abstract AP2.

Johnston et al., "Dosage-sensitive function of retinoblastoma related and convergent epigenetic control are required during the *Arabidopsis* life cycle," *PLoS Genet*, 2010, 6(6):e1000988.

Jorgensen et al., "Chalcone synthase cosuppression phenotypes in petunia flowers: comparison of sense versus antisense constructs and single copy versus complex T-DNA sequences," *Plant Mol. Biol.*, 1996, 31:957-973.

Julio et al. "Reducing the content of nornicotine in tobacco via targeted mutation breeding." *Mol. Breeding* 2008. 21:369-381.

Julio et al., "Targeted Mutation Breeding as a tool for tobacco crop improvement," presentation made in Oct. 2008.

Kafri et al., "The regulatory utilization of genetic redundancy through responsive backup circuits," *Proc Natl Acad Sci USA*, 2006, 103(31):11653-11658.

Kempin et al., "Targeted disruption in *Arabidopsis*," *Nature*, 1997, 389:802-803.

Keskin et al., "A new, structurally nonredundant, diverse data set of protein-protein interfaces and its implications," *Protein Science*, 2004, 13:1043-1055.

Kim et al., "Arabidopsis CYP85A2, a Cytochrome P450, Mediates the Baeyer-Villiger Oxidation of Castasterone to Brassinolide in Brassinosteroid Biosynthesis," *Plant Cell*, 2005, 17:2397-2412.

Klahre et al., "High molecular weight RNAs and small interfering RNAs induce systemic posttranscriptional gene silencing in plants," *Proc. Natl. Acad. Sci.* USA 2002, 99:11981-11986.

Klink and Wolniak, "The utility of RNAi in the study of the plant cytoskeleton," *J. Plant Growth Regulation*, 2000, 19(4):371-384.

Koornneef, "Classical mutagenesis in higher plants," *Mol. Plant Biol.*, 2002, Gilmartin and Bowler (eds.), Oxford University Press, pp. 1-11.

Koshinsky et al., "Cre-lox site-specific recombination between Arabidopsis and tobacco chromosomes," *Plant J.*, 2000, 23:715-722.

Kusaba et al., "Low Glutelin content1: A Dominant Mutation That Suppresses the Glutelin Multigene Family via RNA Silencing in Rice," *Plant Cell* 15:1455-1467 (2003).

Kynast et al., "Dissecting the maize genome by using chromosome addition and radiation hybrid lines," *Proc Natl Acad Sci USA*, 2004, 101(26):9921-9926.

Lazar et al., "Transforming Growth Factor α: Mutation of Aspartic Acid 47 and Leucine 48 Results in Different Biological Activities," *Mol. Cell. Biol.*, 1988, 8(3):1247-1252.

Levin et al., "Methods of double-stranded RNA-mediated gene inactivation in *Arabidopsis* and their use to define an essential gene in methionine biosynthesis," *Plant Mol. Biol.* 44:759-775 (2000).

Lewis, et al. "RNA interference (RNAi)-induced suppression of nicotine demethylase activity reduces levels of a key carcinogen in cured tobacco leaves." *Plant Biotechnology Journal*, 2008. 6:1-9.

Liu et al., "Genetic and transformation studies reveal negative regulation of ERS1 ethylene receptor signaling in *Arabidopsis*," *BMC Plant Biol*, 2010, 10:60-73.

Liu et al., "High-Stearic and High-Oleic Cottonseed Oils Produced by Hairpin RNA-Mediated Post-Transcriptional Gene Silencing," *Plant Physiol*. 129:1732-1743 (2002).

Liu et al., "Identification and characterization of HTD2: a novel gene negatively regulating tiller bud outgrowth in rice," *Planta*, 2009, 230(4):649-658.

Maher, "DNA triple-helix formation: an approach to artificial gene repressors?" *Bioassays*, 1992, 14:807-815.

Mansoor et al. "Engineering novel traits in plants through RNA interference". *Trends in Plant Science*, 2006, 11(11):1-7.

Matthew, "RNAi for plant functional genomics," *Comp Funct Genomics*, 2004, 5:240-244.

McKinney, "Sequence based identification of T-DNA insertion mutations in *Arabidopsis*: actin mutants act2-1 and act4-1," *Plant J.*, 1995, 8:613-622.

Mesnard et al., "Evidence for the Involvement of Tetrahydrofolate in the Demethylation of Nicotine by *Nicotiana plumbaginifolia* Cell-Suspension Cultures," *Planta*, 2002, 214:911-919.

Mette et al., "Transcriptional silencing and promoter methylation triggered by double-stranded RNA," *EMBO J.*, 2000, 19(19):5194-5201.

Mol et al., "Regulation of plant gene expression by antisense RNA," *FEBS Lett.*, 1990, 268:427-430.

Napoli et al., "Introduction of a Chimeric Chalcone Synthase Gene into Petunia Results in Reversible Co-Suppression of Homologous Genes *in trans*," *Plant Cell*, 1990, 2:279-289.

Nawrath and Métraux, "Salicylic Acid Induction-Deficient Mutants of Arabidopsis Express *PR-2* and *PR-5* and Accumulate High Levels of Camalexin after Pathogen Inoculation," *Plant Cell*, 1999, 11:1393-1404.

Needleman and Wunsch, "A General Method Applicable to the Search for Similarities in the Amino Acid Sequence of Two Proteins," *J. Mol. Biol.*, 1970, 48:443-453.

Nelson et al., "Comparative Genomics of Rice and *Arabidopsis*. Analysis of 727 Cytochrome P450 Genes and Pseudogenes from a Monocot and a Dicot," *Plant Physiology*, 2004, 135:756-772.

Nelson et al., "Comparison of cytocrhome P450 (*CYP*) genes from the mouse and human genomes, including nomenclature recommendations for genes, pseudogenes and alternative-splice variants," *Pharmacogenetics*, 2004, 14(1):1-18.

Nishihara et al., "Flavanoid components and flower color change in transgenic tobacco plants by suppression of chalcone isomerase gene," *FEBS Lett*. 579:6074-6078 (2005).

Ogita et al., "Application of RNAi to confirm theobromine as the major intermediate for caffeine biosynthesis in coffee plants with potential for construction of decaffeinated varieties," *Plant Mol. Biol.* 54:931-941 (2004).

Ohshima et al., Nucleotide sequence of the PR-1 gene of *Nicotiana tabacum*, *FEBS Letters*, 1987, 225(1,2):243-246.

Oliver et al., "Inhibition of tobacco NADH-hydroxypyruvate reductase by expression of a heterologous antisense RNA derived from a cucumber cDNA: Implications for the mechanism of action of antisense RNAs," (1993). *Mol Gen Genet* 239(3): 425-434.

Pearson and Lipman, "Improved tools for biological sequence comparison," *Proc. Natl. Acad. Sci. USA*, 1988, 85:2444-2448.

Pickett and Meeks-Wagner, "Seeing Double: Appreciating Genetic Redundancy," *Plant Cell*, 1995, 7:1347-1356.

Plant Variety Protection Office (USDA-AMS, Beltsville, MD, http://www.ars-grin.gov/cgi-bin/npgs/html/pvp.pl?Tobacco, accessed Feb. 2009), 2 pages.

Puchta et al., "Two different but related mechanisms are used in plants for the repair of genomic double-strand breaks by homologous recombination," *Proc. Natl. Acad. Sci. USA*, 1996, 93:5055-5060.

Qin et al., "Cre recombinase-mediated site-specific recombination between plant chromosomes," *Proc. Natl. Acad. Sci. USA*, 1994, 91:1706-1710.

Qiu et al. "A computational study of off-target effects of RNA interference." *Nucleic Acids Research*. 2005. 33(6)1834-1847.

Ralston et al., "Cloning, Heterologous Expression, and Functional Characterization of 5-*epi*-Aristolochene-1,3-Dihydroxylase from Tobacco (*Nicotiana tabacum*)," *Arch. Biochem. Biophys.*, 2001, 393(2):222-235.

Reid and Haley, "Studies on the Fermentation of Tobacco 1. The Microflora of Cured and Fermenting Cigar-leaf Tobacco," Bulletin 356, 1938, Pennsylvania Agricultural Experiment Station, State College, PA.

Rodermel et al., "Nuclearorganelle interactions: Nuclear antisense gene inhibits ribulose bisphosphate carboxylase enzyme levels in transformed tobacco plants," *Cell*, 1988, 55:673-681.

Rohr et al., "Tandem inverted repeat system for selection of effective transgenic RNAi strains of *Chlamydomonas*," *Plant J.*, 2004, 40:611-621.

Salehuzzaman et al., "Isolation and characterization of a cDNA encoding granule-bound starch synthase in cassava (*Manihot esculenta Crantz*) and its antisense expression in potato," (1993) *Plant Mol Biol* 23(5): 947-962.

Schenk et al., "Coordinated plant defense responses in *Arabidopsis* revealed by microarray analysis," *Proc. Natl. Acad. Sci. USA*, 2000, 97(21):11655-11660.

Schnable et al., "Genetic recombination in plants," *Curr. Opinions Plant Biol.*, 1998, 1:123-129.

Schopfer and Ebel, "Identification of elicitor-induced cytochrome P450s of soybean (*Glycine max* L.) using differential display of mRNA," *Mol. Gen. Genet.*, 1998, 258:315-322.

Shah et al., "Expression of Silent Mutations in Disease Phenotype" Abstract for presentation at 11th International Congress of Human Genetics, 1 page, (2006).

Shen et al., "Resistance Gene Candidates Identified by PCR with Degenerate Oligonucleotide Primers Map to Clusters of Resistance Genes in Lettuce," *Molecular Plant-Microbe Interactions*, 1998, 11(8):815-823.

Siminszky et al., "Conversion of nicotine to nornicotine in *Nicotiana tabacum* is mediated by CYP82E4, a cytochrome P450 monooxygenase," *PNAS*, 2005, 102(41):14919-14924.

Sinvany-Villalobo et al., "Expression in Multigene Families. Analysis of Chloroplast and Mitochondrial Proteases," *Plant Physiol*, 2004, 135:1336-1345.

Skarnes et al., "Entrapment vectors: a new tool for mammalian genetics," *BioTechnology*, 1990, 8:827-831.

Smith and Waterman, "Comparison of Biosequences," *Adv. Appl. Math.*, 1981, 2:482-489.
Smith et al., "Total silencing by intron-spliced hairpin RNAs," *Nature*, 2000, 407:319-320.
Spradling et al., "Gene disruptions using *P* transposable elements: An integral component of the *Drosophila* genome project," *Proc. Natl. Acad. Sci. USA*, 1995, 92:10824-10830.
Stalberg et al., "Deletion analysis of a 2S seed storage protein promoter of *Brassica napus* in transgenic tobacco," *Plant Mol. Biol.*, 1993, 23:671-683.
Sundaresan et al., "Patterns of gene action in plant development revealed by enhancer trap and gene trap transposable elements," *Genes Dev.*, 1995, 9:1797-1810.
Sureka et al., "Positive Feedback and Noise Activate the Stringent Response Regulator Rel in Mycobacteria," *PLoS One*, 2008, 3(3).
Takemoto et al., "Molecular Cloning of a Defense-Response-Related Cytochrome P450 Gene from Tobacco," *Plant Cell Physiol.*, 1999, 40(12):1232-1242.
Takken et al. "A functional cloning strategy, based on a binary PVX-expression vector, to isolate HR-inducing cDNAs of plant pathogens," *The Plant Journal*, 2000, 24(2):275-283.
Tang et al., "Using RNAi to improve plant nutritional value: from mechanism to application," TRENDS in Biotechnology, 22(9):463-69 (2004).
Tavernarakis et al., "Heritable and inducible genetic interference by double-stranded RNA encoded by transgenes," *Nat. Genet.*, 2000, 24:180-183.
Temple et al., "Modulation of glutamine synthetase gene expression in tobacco by the introduction of an alfalfa glutamine synthetase gene in sense and antisense orientation: molecular and biochemical analysis," (1993). Mol Gen Genet 236(2-3): 315-25.
Thomas et al., "Size constraints for targeting post-transcriptional gene silencing and for RNA-directed methylation in *Nicotiana benthamiana* using a potato virus X vector," *Plant J.*, 2001, 25(4):417-425.
Thornton et al., "From structure to function: Approaches and limitations," *Nature Structural Biology, Structural Genomics Supplement*, Nov. 2000, pp. 991-994.
Till et al., "Discovery of induced point mutations in maize genes by TILLING," *BMC Plant Biology*, 2004, 4:12.
Tobacco in the United States, U.S. Department of Agriculture, 32 pages, (1979).
Toscano et al., "A silent mutation (2939G>A, exon 6; CYP2D6*59) leading to impaired expression and function of CYP2D6," *Pharmacogenet Genomics*, 2006, 16(10):767-7670.
Travella, et al. "RNA Interference-Based Gene Silencing as an Efficient Tool for Functional Genomics in Hexaploid Bread Wheat." *Plant Physiology*. 2006, 142:6-20.
Trevanion et al., "NADP-Malate Dehydrogenase in the $C_4$ Plant *Flaveria bidentis*," (1997) *Plant Physiol* 113(4): 1153-1165.
Turner and Schuch, "Post-transcriptional gene-silencing and RNA interference: genetic immunity, mechanisms and applications," *J. Chem. Technol. Biotechnol.*, 2000, 75:869-882.
United States, "Tobacco in the United States," Miscellaneous Publication No. 867, 1979, U.S. Dept. of Agriculture, Agricultural Marketing Service.
Vaistij et al., "Spreading of RNA Targeting and DNA Methylation in RNA Silencing Requires Transcription of the Target Gene and a Putative RNA-Dependent RNA Polymerase," *Plant Cell* 14:857-867 (2002).
Van der Krol et al., "An anti-sense chalcone synthase gene in transgenic plants inhibits flower pigmentation," (1988) *Nature* 333: 866-869.
van der Krol et al., "Antisense genes in plants: an overview," *Gene*, 1988, 72:45-50.
Veena et al., "Glyoxalase I from *Brassica juncea*: molecular cloning, regulation and its overexpression confer tolerance in transgenic tobacco under stress," (1999). *Plant Journal* 17(4): 385-395.
Verdaguer et al., "Functional organization of the cassava vein mosaic virus (CsVMV) promoter," *Plant Mol. Biol.*, 1998, 37(6):1055-1067.
Verkerk, "Chimerism of the tomato plant after seed irradiation with fast neutrons," *Neth J. Agric. Sci.*, 1971, 19:197-203.

Voss et al., "The role of enhancers in the regulation of cell-type-specific transcriptional control," *Trends Biochem. Sci.*, 1986, 11:287.
Wang and Wagner, "Elucidation of the functions of genes central to diterpene metabolism in tobacco trichomes using posttranscriptional gene silencing," *Planta*, 2003, 216:686-691.
Wang et al., "Isolation and characterization of the CYP71D16 trichome-specific promoter from Nicotania tabacum L" *Journal of Experimental Botany*, 2002, 53(376):1891-1897.
Wang et al., "Suppression of a P450 hydroxylase gene in plant trichome glands enhances natural-product-based aphid resistance," *Nat. Biotechnol.*, 2001, 19:371-374.
Waterhouse et al., "Virus resistance and gene silencing in plants can be induced by simultaneous expression of sense and antisense RNA," *Proc. Natl. Acad. Sci. USA*, 1998, 95:13959-13964.
Weigel and Nilsson, "A developmental switch sufficient for flower initiation in diverse plants," *Nature*, 1995, 377:495-500.
Weising et al., "Foreign Genes in Plants: Transfer, Structure, Expression, and Applications," *Ann. Rev. Genet.*, 1988, 22:421-477.
Werck-Reichhart and Feyereisen, "Cytochromes P450: a success story," *Genome Biology*, 2000, 1(6):3003.1-3003.9.
Werck-Reichhart et al., "Cytochromes P450," *The Arabidopsis Book*, 2002, American Society of Plant Biologists, 28 pages.
Wernsman and Matzinger, "Relative stability of alleles at the nicotine conversion locus of tobacco," *Tobacco Sci.*, 1970, 14:34-36.
Wesley et al., "Construct design for efficient, effective, and high-throughput gene silencing in plants," *Plant J*, 2001, 27(6):581-590.
Wetmur, "DNA Probes: Applications of the Principles of Nucleic Acid Hybridization," Crit. Rev. Biol. Mol. Biol., 1991, 26:227-259.
Whitbred and Schuler, "Molecular Characterization of *CYP73A9* and *CYP82A1* P450 Genes Involved in Plant Defense in Pea," *Plant Physiol.*, 2000, 124:47-58.
Wu et al. "Herbivory Rapidly Activates MAPK Signaling in Attacked and Unattacked Leaf Regions but Not between Leaves of *Nicotiana attenuata*." *The Plant Cell*. 2007. 19:1096-1122.
Xiong et al., "Different effects on ACC oxidase gene silencing triggered by RNA interference in transgenic tomato," *Plant Cell* 23:639-646 (2004).
Xu et al. "Computational Estimation and Experimental Verification of Off-Target Silencing during Posttranscriptional Gene Silencing in Plants". *Plant Physiology*. 2006, 142:429-440.
Xu et al., "Biochemical and molecular characterizations of nicotine demethylase in tobacco," *Physiologia Plantarum*, 2006, 0:1-13.
Authorized Officer Anne R. Kubelik, PCT/US07/87386, International Search Report and Written Opinion of the International Searching Authority, mailed Sep. 10, 2008, 8 pages.
Authorized Officer Nora Lindner, PCT/US07/87386, International Preliminary Report on Patentability, issued Jun. 16, 2009, 5 pages.
Callis et al., "Introns increase gene expression in cultured maize cells," *Genes and Dev.*, 1987, 1:1183-1200
Dekeyser et al., "Transient Gene Expression in Intact and Organized Rice Tissues," *Plant Cell*, 1990, 2:591-602.
Fang et al., "Multiple cis regulatory elements for maximal expression of the cauliflower mosaic virus 35S promoter in transgenic plants," *Plant Cell*, 1989, 1:141-150.
Fromm et al., "An octopine synthase enhancer element directs tissue-specific expression and binds ASF-1, a factor from tobacco nuclear extracts," *Plant Cell*, 1989, 1:977-984.
Maniatis et al., "Regulation of inducible and tissue-specific gene expression," *Science*, 1987, 236:1237-1245.
Maquat, "Nonsense-mediated mRNA decay," *Curr. Biol.*, 2002, 12(6):R196-R197.
Odell et al., "Identification of DNA sequences required for activity of the cauliflower mosaic virus 35S promoter," *Nature*, 1985, 313:810-812.
Vaucheret et al., "Post-transcriptional gene silencing in plants," *J. Cell Sci.*, 2001, 114:3083-3091.
Xu et al., "Biochemical and molecular characterization of nicotine demethylase in tobacco," *Physiologia Plantarum*, 2007, 129(2):307-319.

* cited by examiner

Figure 1
A.
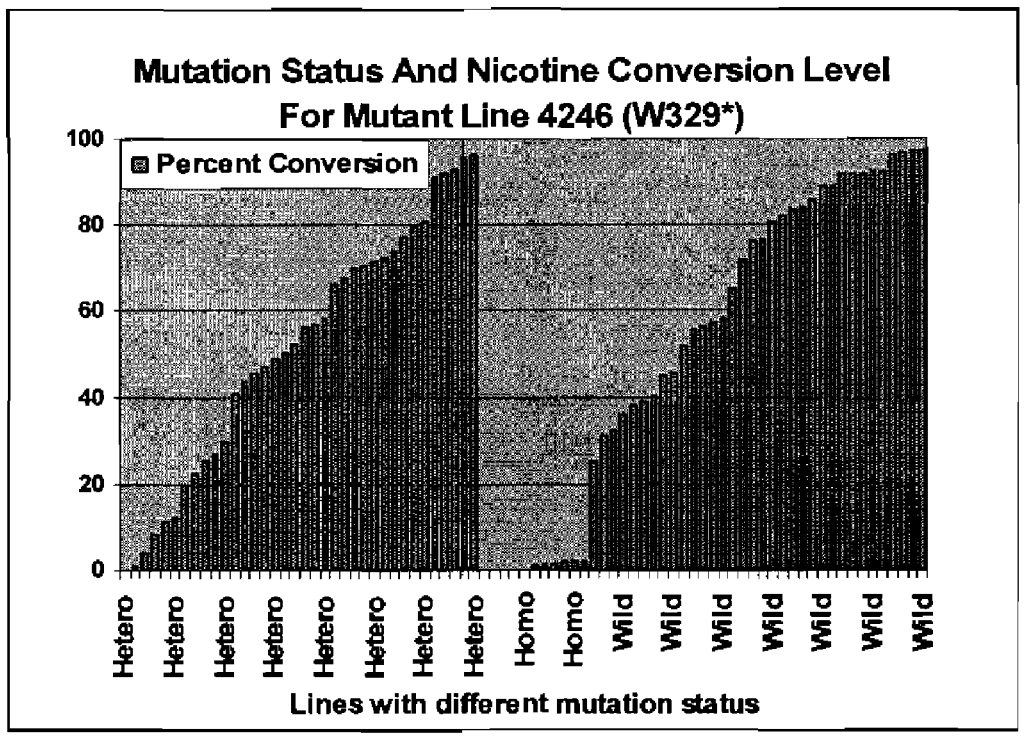
B.
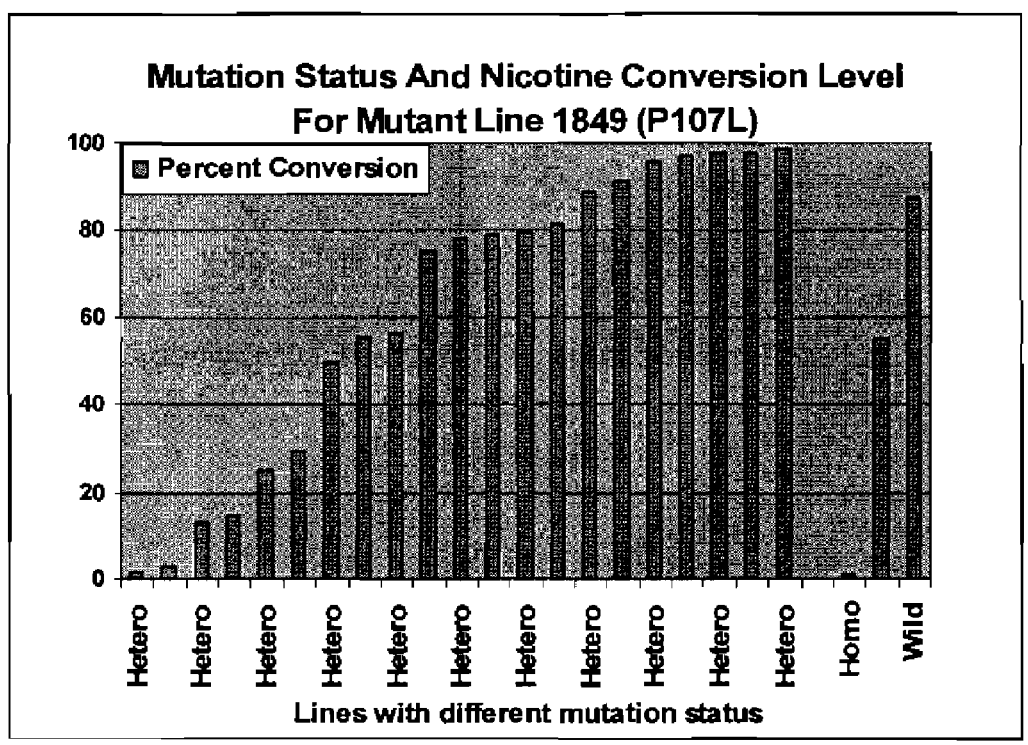

Figure 1, continued
C.
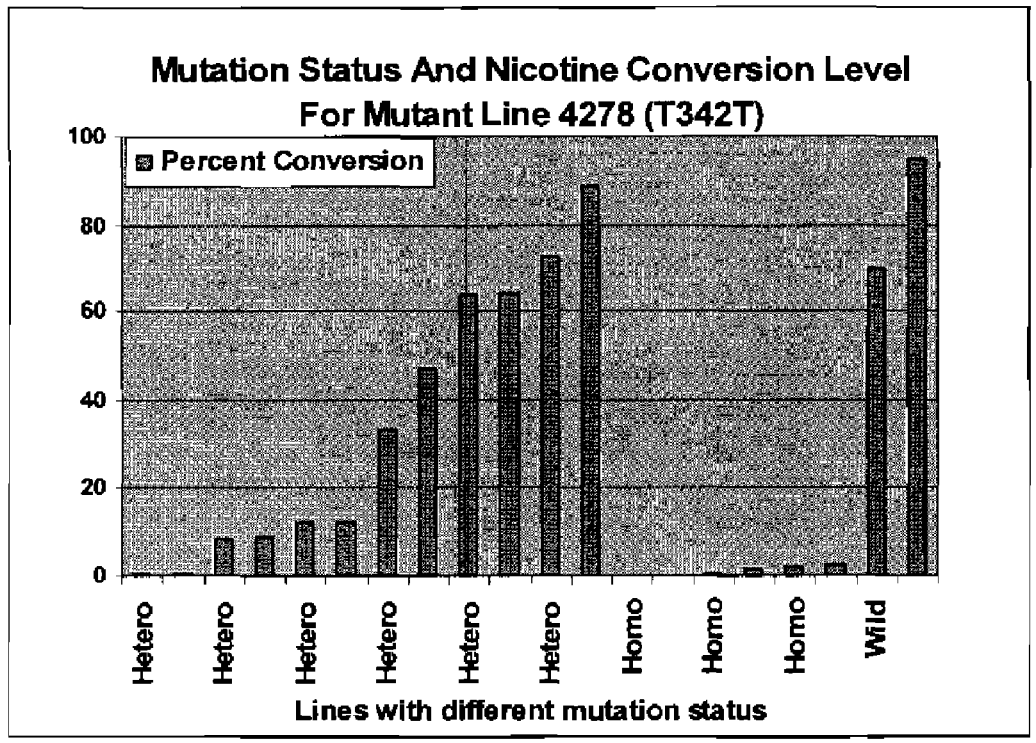
D.
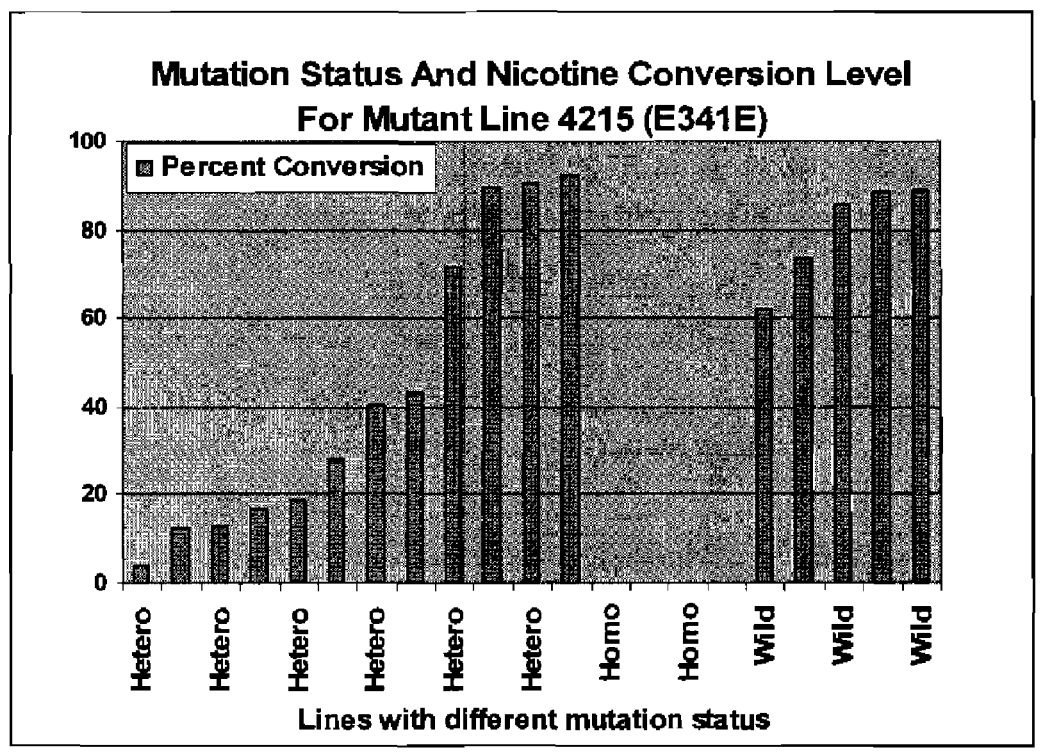

Figure 1, continued
E.
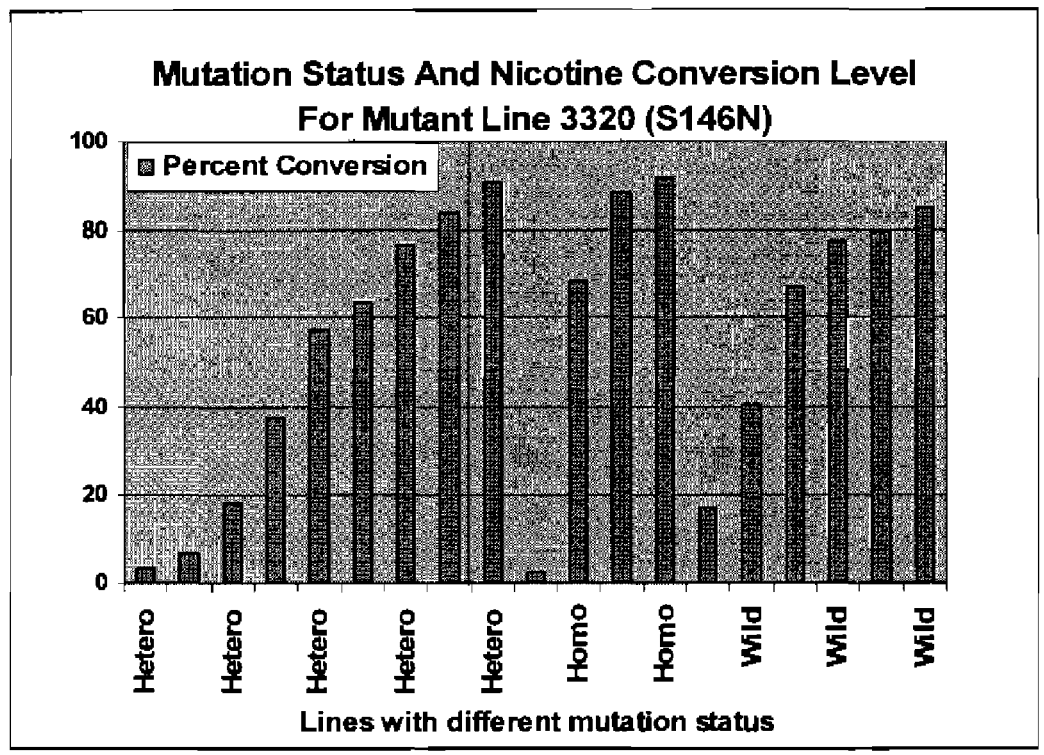
F.
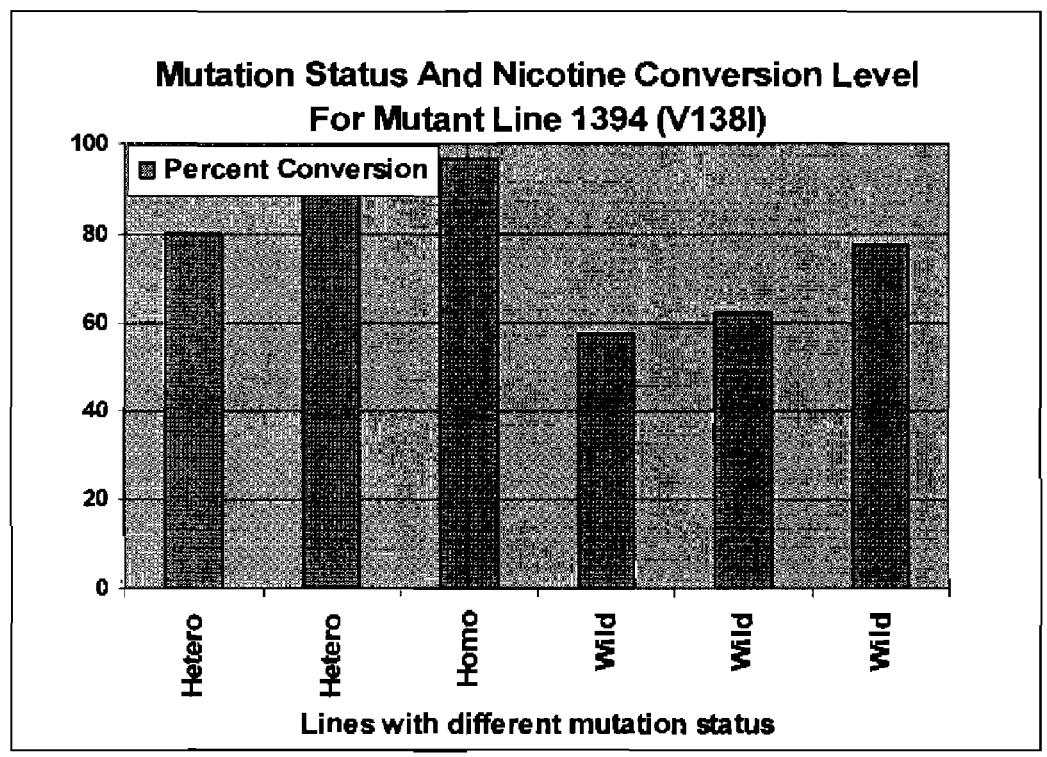

Figure 2

```
   1                                         ATGCTTTCTCCCATAGAAGCCA
                                              M  L  S  P  I  E  A    7
  23 TTGTAGGACTAGTAACCTTCACATTTCTCTTCTTCTTCCTATGGACAAAAAAATCTCAAA
      I  V  G  L  V  T  F  F  F  L  F  F  F  L  W  T  K  K  S  Q    27
                   Membrane Binding Region
  83 AACCTTCAAAACCCTTACCACCGAAAATCCCCGGAGGATGGCCGGTAATCGGCCATCTTT
      K  P  S  K  P  L  P  P  K  I  P  G  G  W  P  V  I  G  H  L    47
 143 TCCACTTCAATGACGACGGCGACGACCGTCCATTAGCTTCGAAAACTCGGAGACTTAGCTG
      F  H  F  N  D  D  G  D  D  R  P  L  A  R  K  L  G  D  L  A    67
 203 ACAAATACGGCCCCGTTTTCACTTTTCGGCTAGGCCTTCCCCTTGTCTTAGTTGTAAGCA
      D  K  Y  G  P  V  F  T  F  R  L  G  L  P  L  V  L  V  V  S    87
 263 GTTACGAAGCTGTAAAAGACTGTTTCTCTACAAATGACGCCATTTTTTCCAATCGTCCAG
      S  Y  E  A  V  K  D  C  F  S  T  N  D  A  I  F  S [N  R  P]  107
 323 CTTTTCTTTACGGCGATTACCTTGGCTACAATAATGCCATGCTATTTTGGCCAATTACG
     [A  F  L  Y  G  D  Y  L  G  Y  N  N  A  M  L  F  L  A  N  Y]  127
                  SRS-1
 383 GACCTTACTGGCGAAAAAATCGAAAATTAGTTATTCAGGAAGTTCTCTCCGCTAGTCGTC
     [G  P] Y  W  R  K  N  R  K  L  V  I  Q  E  V  L  S  A  S  R   147
 443 TCGAAAAATTCAAACACGTGAGATTTGCAAGAATTCAAGCGAGCATTAAGAATTTATATA
      L  E  K  F  K  H  V  R  F  A  R  I  Q  A  S  I  K  N  L  Y   167
 503 CTCGAATTGATGGAAATTCGAGTACGATAAATTTAACTGATTGGTTAGAAGAATTGAATT
      T  R  I  D  G  N  S  S  T  I  N  L  T  D  W  L  E  E  L  N   187
 563 TTGGTCTGATCGTGAAGATGATCGCTGGAAAAAATTATGAATCCGGTAAAGGAGATGAAC
      F  G  L  I  V  K  M  I  A  G  K  N  Y  E  S  G  K  G  D  E   207
 623 AAGTGGAGAGATTTAAGAAAGCGTTTAAGGATTTATGATTTTATCAATGGAGTTTGTGT
      Q  V  E  R [F  K  K  A  F  K  D  F  M] I  L  S  M  E  F  V   227
                  SRS-2
 683 TATGGGATGCATTTCCAATTCCATTATTTAAATGGGTGGATTTTCAAGGGCATGTTAAGG
      L  W  D  A  F  P  I  P  L  F  K  W  V  D  F  Q  G  H  V  K   247
 743 CTATGAAAAGGACTTTTAAAGATATAGATTCTGTTTTTCAGAATTGGTTAGAGGAACATA
      A [M  K  R  T  F  K  D  I] D  S  V  F  Q  N  W  L  E  E  H   267
         SRS-3
 803 TTAATAAAAGAGAAAAAATGGAGGTTAATGCAGAAGGGAATGAACAAGATTTCATTGATG
      I  N  K  R  E  K  M  E  V  N  A  E  G  N  E  Q  D  F  I  D   287
 863 TGGTGCTTTCAAAAATGAGTAATGAATATCTTGGTGAAGGTTACTCTCGTGATACTGTCA
      V  V  L  S  K  M  S  N  E  Y  L  G  E  G  Y  S  R  D  T  V   307
 923 TTAAAGCAACGGTGTTTgtaagttcatctgtcattttcatttattcacttttattttga
      I  K  A  T [V  F]                                             313
 983 ggagcagacatgttaataataatttggagcaactgtaaagttatctatgtgtacaggttc
1043 gagcctcaggtgcaaccactaatgcttgtattagattatgttgtctgcatcatacccta
1103 attggagtgtggctcttcccgaaccctgcaatgctggatgctggatgctttatgtatcag
1163 actgacctttttgttaaactatctaaatactaaggatgatttaataaaaatatagaatgg
1223 taaacagaaaaagatgagattatttttggggctatatggattcgcccgggctttgggagg
1283 taaacggtatctaccagttgagactttactccagaactttatctcgagagctctgaata
1343 aaaatgaaatagtatttaccactccaaaatctttgatggtaaaaagatgagatataacct
1403 cttataattgattgaaccacgttgatagaataaaacttctttactcccattcagcataag
1463 aaaaatgaaaccaaacggaattcttctctttttaggggggaaattccttaattgcttgtt
1523 gaatatagattcatgtcgttattctatttttaataatgatgaaaatcaatatagtcaaag
1583 ttaatacttatgtcatttggtttgcggacaagttatattggaactatataatacgtctat
1643 tatagaatagtgattatttagaggatatacatttttttttggataaatatttgatttattg
1703 gattaaaaatagaatatacaggtaaggtctaaaacgtgtgtttgcttttacactaaataa
1763 acttgacctcgtacaattctaagaaaatatttgaaataaatgaattattttattgttaat
1823 caattaaaaaaatcatagtatagatgagatgtgtgcatacttgacaataactatactaac
```

```
1883 taaaacaaggtatgtgaataattgatattcctttttaattattctttttttccagAGTTT
                                                         S  L    315
1943 GGTCTTGGATGCAGCAGACACAGTTGCTCTTCACATAAATTGGGGAATGGCATTATTGAT
      V  L  D  A  A  D  T  V  A  L  H  I  N  W  G  M  A  L  L  I  335
              SRS-4
2003 AAACAATCAAAAGGCCTTGACGAAAGCACAAGAAGAGATAGACACAAAAGTTGGTAAGGA
      N  N  Q  K  A  L  T  K  A  Q  E  E  I  D  T  K  V  G  K  D  355
2063 CAGATGGGTAGAAGAGAGTGATATTAAGGATTGGTATACCTCCAAGCTATTGTTAAAGA
      R  W  V  E  E  S  D  I  K  D  L  V  Y  L  Q  A  I  V  K  E  375
2123 AGTGTTACGATTATATCCACCAGGACCTTTGTTAGTACCACACGAAAATGTAGAAGATTG
      V  L  R  I  Y  P  P  G  P  L  L  V  P  H  E  N  V  E  D  C  395
                    SRS-5
2183 TGTTGTTAGTGGATATCACATTCCTAAAGGGACAAGATTATTCGCAAACGTCATGAAACT
      V  V  S  G  Y  H  I  P  K  G  T  R  L  F  A  N  V  M  K  L  415
2243 GCAACGTGATCCTAAACTCTGGTCTGATCCTGATACTTTCGATCCAGAGAGATTCATTGC
      Q  R  D  P  K  L  W  S  D  P  D  T  F  D  P  E  R  F  I  A  435
2303 TACTGATATTGACTTTCGTGGTCAGTACTATAAGTATATCCCGTTTGGTTCTGGAAGACG
      T  D  I  D  F  R  G  Q  Y  Y  K  Y  I  P  F  G  S  G  R  R  455
2363 ATCTTGTCCAGGGATGACTTATGCATTGCAAGTGGAACACTTAACAATGGCACATTTGAT
      S  C  P  G  M  T  Y  A  L  Q  V  E  H  L  T  M  A  H  L  I  475
2423 CCAAGGTTTCAATTACAGAACTCCAAATGACGAGCCCTTGGATATGAAGGAAGGTGCAGG
      Q  G  F  N  Y  R  T  P  N  D  E  P  L  D  M  K  E  G  A  G  495
                                                       SRS-6
2483 CATAACTATACGTAAGGTAAATCCTGTGGAACTGATAATAGCGCCTCGCCTGGCACCTGA
      I  T  I  R  K  V  N  P  V  E  L  I  I  A  P  R  L  A  P  E  515
2543 GCTTTATTAA
      L  Y                                                        517
```

Figure 2, continued

SEQUENCE LISTING

```
<160> NUMBER OF SEQ ID NOS: 17

<210> SEQ ID NO 1
<211> LENGTH: 2552
<212> TYPE: DNA
<213> ORGANISM: Nicotiana tabacum

<400> SEQUENCE: 1
atgctttctc ccatagaagc cattgtagga ctagtaacct tcacatttct cttcttcttc      60
ctatggacaa aaaaatctca aaaaccttca aaacccttac caccgaaaat ccccggagga     120
tggccggtaa tcggccatct tttccacttc aatgacgacg gcgacgaccg tccattagct     180
cgaaaactcg gagacttagc tgacaaatac ggccccgttt tcacttttcg gctaggcctt     240
ccccttgtct tagttgtaag cagttacgaa gctgtaaaag actgtttctc tacaaatgac     300
gccatttttt ccaatcgtcc agcttttctt tacggcgatt accttggcta caataatgcc     360
atgctatttt tggccaatta cggaccttac tggcgaaaaa atcgaaaatt agttattcag     420
```

-continued

| | | | |
|---|---|---|---|
| gaagttctct | ccgctagtcg | tctcgaaaaa ttcaaacacg tgagatttgc aagaattcaa | 480 |
| gcgagcatta | agaatttata | tactcgaatt gatggaaatt cgagtacgat aaatttaact | 540 |
| gattggttag | aagaattgaa | ttttggtctg atcgtgaaga tgatcgctgg aaaaaattat | 600 |
| gaatccggta | aaggagatga | acaagtggag agatttaaga aagcgtttaa ggattttatg | 660 |
| attttatcaa | tggagtttgt | gttatgggat gcatttccaa ttccattatt taaatgggtg | 720 |
| gattttcaag | gcatgttaa | ggctatgaaa aggactttta agatatagaa ttctgttttt | 780 |
| cagaattggt | tagaggaaca | tattaataaa agagaaaaaa tggaggttaa tgcagaaggg | 840 |
| aatgaacaag | atttcattga | tgtggtgctt tcaaaaatga gtaatgaata tcttggtgaa | 900 |
| ggttactctc | gtgatactgt | cattaaagca acggtgtttg taagttcatc tgtcattttt | 960 |
| catttattca | cttttatttt | gaggagcaga catgttaata taatttgga gcaactgtaa | 1020 |
| agttatctat | gtgtacaggt | tcgagcctca ggtgcaacca ctaatgcttg tattagatta | 1080 |
| tgttgtctgc | atcataccc | taattggagt gtggctcttc ccgaaccctg caatgctgga | 1140 |
| tgctggatgc | tttatgtatc | agactgacct ttttgttaaa ctatctaaat actaaggatg | 1200 |
| atttaataaa | aatatagaat | ggtaaacaga aaaagatgag attattttg gggctatatg | 1260 |
| gattcgcccg | ggctttggga | ggtaaaacgg tatctaccag ttgagacttt actccagaac | 1320 |
| tttatctcga | gagctctgaa | taaaaatgaa atagtattta ccactccaaa atctttgatg | 1380 |
| gtaaaaagat | gagatataac | ctcttataat tgattgaacc acgttgatag aataaaactt | 1440 |
| ctttactccc | attcagcata | agaaaaatga aaccaaacgg aattcttctc ttttttaggg | 1500 |
| ggaaattcct | taattgcttg | ttgaatatag attcatgtcg ttattctatt tttaataatg | 1560 |
| atgaaaatca | atatagtcaa | agttaatact tatgtcattt ggtttgcgga caagttatat | 1620 |
| tggaactata | taatacgtct | attatagaat agtgattatt tagaggatat acattttttt | 1680 |
| tggataaata | tttgatttat | tggattaaaa atagaatata caggtaaggt ctaaaacgtg | 1740 |
| tgtttgctt | tacactaaat | aaacttgacc tcgtacaatt ctaagaaaat atttgaaata | 1800 |
| aatgaattat | tttattgtta | atcaattaaa aaaatcatag tatagatgag atgtgtgcat | 1860 |
| acttgacaat | aactatacta | actaaaacaa ggtatgtgaa taattgatat tcctttttta | 1920 |
| attattcttt | tttccagagt | ttggtcttgg atgcagcaga cacagttgct cttcacataa | 1980 |
| attggggaat | ggcattattg | ataaacaatc aaaaggcctt gacgaaagca caagaagaga | 2040 |
| tagacacaaa | agttggtaag | gacagatggg tagaagagag tgatattaag gatttggtat | 2100 |
| acctccaagc | tattgttaaa | gaagtgttac gattatatcc accaggacct ttgttagtac | 2160 |
| cacacgaaaa | tgtagaagat | tgtgttgtta gtggatatca cattcctaaa gggacaagat | 2220 |
| tattcgcaaa | cgtcatgaaa | ctgcaacgtg atcctaaact ctggtctgat cctgatactt | 2280 |
| tcgatccaga | gagattcatt | gctactgata ttgactttcg tggtcagtac tataagtata | 2340 |
| tcccgtttgg | ttctggaaga | cgatcttgtc cagggatgac ttatgcattg caagtggaac | 2400 |
| acttaacaat | ggcacatttg | atccaaggtt tcaattacag aactccaaat gacgagccct | 2460 |
| tggatatgaa | ggaaggtgca | ggcataacta tacgtaaggt aaatcctgtg gaactgataa | 2520 |
| tagcgcctcg | cctggcacct | gagctttatt aa | 2552 |

<210> SEQ ID NO 2
<211> LENGTH: 517
<212> TYPE: PRT
<213> ORGANISM: Nicotiana tabacum -continued

<400> SEQUENCE: 2

Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

```
Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
            515

<210> SEQ ID NO 3
<211> LENGTH: 517
<212> TYPE: PRT
<213> ORGANISM: Nicotiana tabacum

<400> SEQUENCE: 3

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Met Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270
```

```
Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
        290                 295                 300

Asp Thr Val Ile Glu Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
                340                 345                 350

Cys Lys Asp Arg Trp Val Glu Glu Ser Asp Ile Lys Asp Leu Val Tyr
                355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Pro Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515

<210> SEQ ID NO 4
<211> LENGTH: 517
<212> TYPE: PRT
<213> ORGANISM: Nicotiana tabacum

<400> SEQUENCE: 4

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Asp Arg Pro Leu Ala Arg Lys Leu Gly
            50                  55                  60

Asp Leu Ala Asp Lys Tyr Gly Pro Val Phe Thr Phe Arg Leu Gly Leu
65              70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125
```

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Leu
                405                 410                 415

Arg Asp Pro Lys Leu Trp Pro Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 5
<211> LENGTH: 316
<212> TYPE: DNA
<213> ORGANISM: Artificial Sequence

```
<220> FEATURE:
<223> OTHER INFORMATION: synthetically generated fragment

<400> SEQUENCE: 5
ctgcaacgtg atcctaaact ctggtctgat cctgatactt tcgatccaga gagattcatt     60
gctactgata ttgactttcg tggtcagtac tataagtata tcccgtttgg ttctggaaga    120
cgatcttgtc cagggatgac ttatgcattg caagtggaac acttaacaat ggcacatttg    180
atccaaggtt tcaattacag aactccaaat gacgagccct ggatatgaa ggaaggtgca     240 ggcataacta tacgtaaggt aaatcctgtg aactgataa tagcgcctcg cctggcacct      300
gagctttatt aaaacc                                                     316

<210> SEQ ID NO 6
<211> LENGTH: 179
<212> TYPE: DNA
<213> ORGANISM: Artificial Sequence
<220> FEATURE:
<223> OTHER INFORMATION: synthetically generated fragment

<400> SEQUENCE: 6
ggtctgatcg tgaagatgat cgctggaaaa aattatgaat ccggtaaagg agatgaacaa     60
gtggagagat ttaagaaagc gtttaaggat tttatgattt tatcaatgga gtttgtgtta    120
tgggatgcat ttccaattcc attatttaaa tgggtggatt tcaagggca tgttaaggc     179

<210> SEQ ID NO 7
<211> LENGTH: 254
<212> TYPE: DNA
<213> ORGANISM: Artificial Sequence
<220> FEATURE:
<223> OTHER INFORMATION: synthetically generated fragment

<400> SEQUENCE: 7
gggatgcatt tccaattcca ttatttaaat gggtggattt tcaagggcat gttaaggcta     60
tgaaaaggac ttttaaagat atagattctg tttttcagaa ttggttagag aacatatta    120 ataaaagaga aaaatggag gttaatgcag aagggaatga acaagatttc attgatgtgg    180
tgctttcaaa aatgagtaat gaatatcttg gtgaaggtta ctctcgtgat actgtcatta    240
aagcaacggt gttt                                                       254

<210> SEQ ID NO 8
<211> LENGTH: 120
<212> TYPE: DNA
<213> ORGANISM: Artificial Sequence
<220> FEATURE:
<223> OTHER INFORMATION: synthetically generated fragment

<400> SEQUENCE: 8
ttggatatga aggaaggtgc aggcataact atacgtaagg taaatcctgt ggaactgata     60
atagcgcctc gcctggcacc tgagctttat taaaacctaa gatctttcat cttggttgat    120

<210> SEQ ID NO 9
<211> LENGTH: 998
<212> TYPE: DNA
<213> ORGANISM: Artificial Sequence
<220> FEATURE:
<223> OTHER INFORMATION: synthetically generated fragment

<400> SEQUENCE: 9
gtaagttcat ctgtcatttt tcatttattc acttttattt tgaggagcag acatgttaat     60
aataatttgg agcaactgta aagttatcta tgtgtacagg ttcgagcctc aggtgcaacc    120
```

```
actaatgctt gtattagatt atgttgtctg catcataccc ctaattggag tgtggctctt      180
cccgaaccct gcaatgctgg atgctggatg ctttatgtat cagactgacc tttttgttaa      240
actatctaaa tactaaggat gatttaataa aaatatagaa tggtaaacag aaaaagatga      300
gattattttt ggggctatat ggattcgccc gggctttggg aggtaaaacg gtatctacca      360
gttgagactt tactccagaa ctttatctcg agagctctga ataaaatga aatagtattt      420 accactccaa aatctttgat ggtaaaaaga tgagatataa cctcttataa ttgattgaac      480
cacgttgata gaataaaact tctttactcc cattcagcat aagaaaatg aaaccaaacg      540 gaattcttct ctttttttagg gggaaattcc ttaattgctt gttgaatata gattcatgtc      600
gttattctat ttttaataat gatgaaaatc aatatagtca aagttaatac ttatgtcatt      660
tggtttgcgg acaagttata ttggaactat ataatacgtc tattatagaa tagtgattat      720
ttagaggata tacattttt ttggataaat atttgattta ttggattaaa aatagaatat      780
acaggtaagg tctaaaacgt gtgtttgctt ttacactaaa taaacttgac ctcgtacaat      840
tctaagaaaa tatttgaaat aaatgaatta ttttattgtt aatcaattaa aaaaatcata      900
gtatagatga gatgtgtgca tacttgacaa taactatact aactaaaaca aggtatgtga      960
ataattgata ttccttttttt aattattctt ttttccag                            998
```

```
<210> SEQ ID NO 10
<211> LENGTH: 431
<212> TYPE: DNA
<213> ORGANISM: Artificial Sequence
<220> FEATURE:
<223> OTHER INFORMATION: synthetically generated fragment

<400> SEQUENCE: 10
gtctgccagt tcagttcgtt gttcacacaa acggtgatac gtacactttt cccggcaata       60
acatacggcg tgacatcggc ttcaaatggc gtatagccgc cctgatgctc catcacttcc      120
tgattattga cccacacttt gccgtaatga gtgaccgcat cgaaacgcag cacgatacgc      180
tggcctgccc aacctttcgg tataaagact tcgcgctgat accagacgtt gcccgcataa      240
ttacgaatat ctgcatcggc gaactgatcg ttaaaactgc ctggcacagc aattgcccgg      300 cttttcttgta acgcgctttc ccaccaacgc tgatcaattc cacagttttc gcgatccaga      360
ctgaatgccc acaggccgtc gagttttttg atttcacggg ttggggtttc tacaggacgt      420
aaactagtca g                                                          431
```

```
<210> SEQ ID NO 11
<211> LENGTH: 155
<212> TYPE: DNA
<213> ORGANISM: Artificial Sequence
<220> FEATURE:
<223> OTHER INFORMATION: synthetically generated fragment

<400> SEQUENCE: 11
gtaataagat cttcaacacc tacaccattt ttttaatcac tactacccat tgcattgaac       60
aaacttccaa gttcttctta gcttcagatt aagaaagtac cctttcttgg ctttgttgat      120
gtggtaccat tgtccattgt cttgtgtgtt tccag                                 155
```

```
<210> SEQ ID NO 12
<211> LENGTH: 1554
<212> TYPE: DNA
<213> ORGANISM: Nicotiana tabacum CYP82E5
```

<400> SEQUENCE: 12

```
atggtttctc ccgtagaagc cattgtagga ctagtaaccc ttacacttct cttctacttc      60
ctatggccca aaaaatttca aataccttca aaaccattac caccgaaaat tcccggaggg     120
tggccggtaa tcggccatct tttctacttc gatgatgacg gcgacgaccg tccattagct     180
cgaaaactcg gagacttagc tgacaaatac ggcccggttt tcactttccg gctaggcctt     240
ccgcttgtgt tagttgtaag cagttacgaa gctgtaaaag actgcttctc tacaaatgac     300
gccatttttct ccaatcgtcc agcttttctt tacggtgaat accttggcta caataatgcc     360
atgctatttt tgacaaaata cggaccttat tggcgaaaaa atagaaaatt agtcattcag     420
gaagttctct ctgctagtcg tctcgaaaaa ttgaagcacg tgagatttgg taaaattcaa     480
acgagcatta agagtttata cactcgaatt gatggaaatt cgagtacgat aaatctaact     540
gattggttag aagaattgaa ttttggtctg atcgtgaaaa tgatcgctgg gaaaaattat     600
gaatccggta aggagatgaa acaagtggag agatttagga aagcgtttaa ggatttttata     660
attttatcaa tggagtttgt gttatgggat gcttttccaa ttccattgtt caaatgggtg     720
gattttcaag gccatgttaa ggccatgaaa aggacattta aggatataga ttctgttttt     780
cagaattggt tagaggaaca tgtcaagaaa agagaaaaaa tggaggttaa tgcacaaggg     840
aatgaacaag atttcattga tgtggtgctt tcaaaaatga gtaatgaata tcttgatgaa     900
ggttactctc gtgatactgt cataaaagca acagtgttta gtttggtctt ggatgctgcg     960
gacacagttg ctcttcacat gaattgggga atggcattac tgataaacaa tcaacatgcc    1020
ttgaagaaag cacaagaaga gatcgataaa aaagttggta aggaaagatg ggtagaagag    1080
agtgatatta aggatttggt ctacctccaa gctattgtta aagaagtgtt acgattatat    1140
ccaccaggac ctttattagt acctcatgaa aatgtagagg attgtgttgt tagtggatat    1200
cacattccta agggactag actattcgcg aacgttatga aattgcagcg cgatcctaaa    1260
ctctggtcaa atcctgataa gtttgatcca gagagattct tcgctgatga tattgactac    1320
cgtggtcagc actatgagtt tatcccattt ggttctggaa gacgatcttg tccggggatg    1380
acttatgcat tacaagtgga acacctaaca atagcacatt tgatccaggg tttcaattac    1440
aaaactccaa atgacgagcc cttggatatg aaggaaggtg caggattaac tatacgtaaa    1500
gtaaatcctg tagaagtgac aattacggct cgcctggcac ctgagcttta ttaa          1554
```

<210> SEQ ID NO 13
<211> LENGTH: 517
<212> TYPE: PRT
<213> ORGANISM: Nicotiana tabacum CYP82E5

<400> SEQUENCE: 13

```
Met Val Ser Pro Val Glu Ala Ile Val Gly Leu Val Thr Leu Thr Leu
 1               5                  10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95
```

```
Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515
```

```
<210> SEQ ID NO 14
<211> LENGTH: 26
<212> TYPE: DNA
<213> ORGANISM: Artificial Sequence
<220> FEATURE:
<223> OTHER INFORMATION: synthetically generated fragment

<400> SEQUENCE: 14
ctaaaactcc ataatggttt ctcccg                                          26

<210> SEQ ID NO 15
<211> LENGTH: 27
<212> TYPE: DNA
<213> ORGANISM: Artificial Sequence
<220> FEATURE:
<223> OTHER INFORMATION: synthetically generated fragment

<400> SEQUENCE: 15
acctgtctat tcctcaaaat cagactg                                         27

<210> SEQ ID NO 16
<211> LENGTH: 26
<212> TYPE: DNA
<213> ORGANISM: Artificial Sequence
<220> FEATURE:
<223> OTHER INFORMATION: synthetically generated fragment

<400> SEQUENCE: 16
gacctcgtac atctctaaga gaaagc                                          26

<210> SEQ ID NO 17
<211> LENGTH: 40
<212> TYPE: DNA
<213> ORGANISM: Artificial Sequence
<220> FEATURE:
<223> OTHER INFORMATION: synthetically generated fragment

<400> SEQUENCE: 17
gcatatatat attagtacaa tcaagataaa acatctaagg                           40
```

TOBACCO PLANTS HAVING REDUCED NICOTINE DEMETHYLASE ACTIVITY

CROSS-REFERENCE TO RELATED APPLICATIONS

This application claims priority under 35 USC §119(e) to U.S. Application No. 61/098,601, filed Sep. 19, 2008. This application also is a continuation-in-part (CIP) and claims benefit under 35 USC §120 of International Application No. PCT/US2007/087386, filed on Dec. 13, 2007, which claims the benefit of U.S. application Ser. No. 11/611,782, filed Dec. 15, 2006. The contents of all applications are incorporated herein by reference for all purposes in their entirety.

BACKGROUND OF THE INVENTION

1. Technical Field

The present invention is generally directed to compositions and methods related to tobacco plants having reduced nicotine demethylase activity.

2. Background Information

Tobacco plants are known to N-demethylate nicotine to form nornicotine, a secondary alkaloid known to be a precursor for the microbial-mediated formation of N-Nitrosonornicotine (hereinafter, "NNN") in cured leaves. The N-demethylation reaction is catalyzed by the enzyme nicotine demethylase (NDM). Current methods to reduce the conversion of the substrate nicotine to the product nornicotine in tobacco have utilized screening to eliminate converter plants from foundation seed lots that are used for commercial seed production. Seed produced directly from screened seed, however, still contains converters.

SUMMARY OF THE INVENTION

Provided herein are compositions and methods related to the production of tobacco plants, hybrids, varieties, and lines having a mutation in a nicotine demethylase gene or expressing a double-stranded RNA comprising a sequence from a nicotine demethylase gene.

Provided herein are tobacco hybrids, varieties, and lines. A tobacco hybrid, variety, or line can comprise plants having a mutation in a nicotine demethylase gene. A plant having a mutation in a nicotine demethylase gene can have a non-converter phenotype, and the progeny of such a plant can have a reversion rate that is reduced at least 2× (e.g., 10× to 1000× or 2× to 100×) compared to the reversion rate of the corresponding tobacco hybrid, variety, or line comprising plants comprising a wild type nicotine demethylase gene. A tobacco hybrid, variety, or line can be a Burley type, a dark type, a flue-cured type, or an Oriental type tobacco. A tobacco hybrid, variety, or line can be a *Nicotiana tabacum* hybrid, variety, or line. A variety can be essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359.

Also provided are tobacco hybrids, varieties, and lines comprising plants having a mutant allele at a nicotine demethylase locus. In certain embodiments, a mutant allele at a nicotine demethylase locus encodes an amino acid sequence selected from the group consisting of SEQ ID NO:2, wherein the tryptophan at amino acid 329 is replaced with a stop codon; SEQ ID NO:2, wherein the proline at amino acid 107 is replaced with a with an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; SEQ ID NO:2, wherein the isoleucine at amino acid 163 is replaced with methionine, the lysine at amino acid 309 is replaced with glutamic acid, the glycine at amino acid 353 is replaced with cysteine, and serine at amino acid 452 is replaced with proline; SEQ ID NO:2, wherein the glutamine at amino acid 416 is replaced with leucine and the serine at amino acid 423 is replaced with proline; SEQ ID NO:2, wherein the isoleucine at amino acid 163 is replaced with methionine, the lysine at amino acid 309 is replaced with glutamic acid, the glycine at amino acid 353 is replaced with cysteine, the glutamine at amino acid 416 is replaced with leucine, the serine at amino acid 423 is replaced with proline, and serine at amino acid 452 is replaced with proline; SEQ ID NO:2, wherein the amino acid sequence comprises three substitutions selected from the group consisting of I163M, L309E, G353C, Q416L, S423P, and S452P; SEQ ID NO:2, wherein an amino acid P107 is deleted; SEQ ID NO:2, wherein at least three amino acids selected from the group consisting of I163, L309, G353, Q416, S423, and S452 are deleted; SEQ ID NO:2, wherein an insertion of one or two amino acids is adjacent to an amino acid selected from the group consisting of P107, I163, L309, G353, Q416, S423, and S452; SEQ ID NO:2, wherein an amino acid at any position from 1 to 328 is replaced with a stop codon; and SEQ ID NO:2, wherein an amino acid at any position from 330 to 457 is replaced with a stop codon. In one particular embodiment, a mutant allele encodes an amino acid sequence comprising the sequence set forth in SEQ ID NO:2, wherein the proline at amino acid 107 is replaced with a leucine.

In other embodiments, a mutant allele comprises a nucleic acid sequence selected from the group consisting of: SEQ ID NO:1, wherein the guanine at nucleic acid +2021 is replaced with an adenine; SEQ ID NO:1, wherein the guanine at nucleic acid +2291 is replaced with an adenine; SEQ ID NO:1, wherein a splice donor is inserted in the intron; and SEQ ID NO:1, wherein a splice acceptor is inserted in the intron. In one particular embodiment, a hybrid, variety, or line is a *Nicotiana tabacum* hybrid, variety, or line. In another embodiment, a variety is essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359.

In certain other embodiments, the invention is directed to methods of making a tobacco plant. In particular embodiments, a method of making a tobacco plant comprises inducing mutagenesis in cells of a Nicotiana species, obtaining one or more plants from said cells, and identifying at least one of such plants that contains a nicotine demethylase gene having at least one mutation. In other embodiments, the method further comprises crossing a plant containing said at least one mutation in a nicotine demethylase gene with a second Nicotiana plant; and selecting progeny of the cross that have the nicotine demethylase gene mutation. In certain embodiments, a mutation comprises a nicotine demethylase gene encoding the amino acid sequence set forth in SEQ ID NO:2, wherein the tryptophan at amino acid 329 is replaced with a stop codon; a nicotine demethylase gene encoding the amino acid sequence set forth in SEQ ID NO:2, wherein the proline at amino acid 107 is replaced with a with an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; a nicotine demethylase gene encoding the amino acid sequence set forth in SEQ ID NO:2, wherein the isoleucine at amino acid 163 is replaced with methionine, the lysine at amino acid 309 is replaced with glutamic acid, the glycine at amino acid 353 is replaced with cysteine, and serine at amino acid 452 is replaced with proline; a nicotine demethylase gene encoding the amino acid sequence set forth in SEQ ID NO:2, wherein the glutamine at amino acid 416 is replaced with leucine and the serine at amino acid 423 is replaced with proline; a nicotine demethylase gene encoding the amino acid sequence set forth in SEQ ID NO:2, wherein the isoleucine at amino acid 163 is replaced with methionine, the lysine at amino acid 309 is replaced with glutamic acid, the glycine at amino acid 353 is replaced with cysteine, the glutamine at amino acid 416 is replaced with leucine, the serine at amino acid 423 is replaced with proline, and serine at amino acid 452 is replaced with proline; a nicotine demethylase gene encoding the amino acid sequence set forth in SEQ ID NO:2, wherein the amino acid sequence comprises three substitutions selected from the group consisting of I163M, L309E, G353C, Q416L, S423P, and S452P; a nicotine demethylase gene encoding the amino acid sequence set forth in SEQ ID NO:2, wherein an amino acid P107 is deleted; a nicotine demethylase gene encoding the amino acid sequence set forth in SEQ ID NO:2, wherein at least three amino acids selected from the group consisting of I163, L309, G353, Q416, S423, and S452 are deleted; a nicotine demethylase gene encoding the amino acid sequence set forth in SEQ ID NO:2, wherein an insertion of one or two amino acids is adjacent to an amino acid selected from the group consisting of P107, I163, L309, G353, Q416, S423, and S452; a nicotine demethylase gene encoding the amino acid sequence set forth in SEQ ID NO:2, wherein an amino acid at any position from 1 to 328 is replaced with a stop codon; a nicotine demethylase gene encoding the amino acid sequence set forth in SEQ ID NO:2, wherein an amino acid at any position from 330 to 457 is replaced with a stop codon in a nicotine demethylase gene comprising the sequence set forth in SEQ ID NO:1, wherein the guanine at nucleic acid +2021 is replaced with an adenine; a nicotine demethylase gene comprising the sequence set forth in SEQ ID NO:1, wherein the guanine at nucleic acid +2291 is replaced with an adenine; a nicotine demethylase gene comprising the sequence set forth in SEQ ID NO:1, wherein a splice donor is inserted in the intron; a nicotine demethylase gene comprising the sequence set forth in SEQ ID NO:1, wherein a splice acceptor is inserted in the intron. In particular embodiments, inducing mutagenesis in cells of a Nicotiana species are in a seed.

In some embodiments, the second tobacco plant exhibits a phenotypic trait such as disease resistance; high yield; high grade index; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves). In still other embodiments, the method further includes self-pollinating or pollinating a male sterile pollen acceptor with a pollen donor capable of being used in production of a hybrid or a male sterile hybrid. Either the male sterile pollen acceptor plant or the pollen donor plant has a mutant allele at a nicotine demethylase locus. In some embodiments, both alleles at the nicotine demethylase locus are mutant alleles.

Also provided herein is cured tobacco material. In certain embodiments, a cured tobacco is made from a hybrid, variety, or line comprising plants having a mutation in a nicotine demethylase gene. In other embodiments, a tobacco plant having a mutation in a nicotine demethylase gene has a non-converter phenotype. In other embodiments, progeny of the plants have a reduced reversion rate as compared to the corresponding hybrid, variety, or line comprising plants having a wild type nicotine demethylase gene. In other embodiments, a cured tobacco is made from a hybrid, variety, or line comprising plants transformed with an RNAi construct comprising a nicotine demethylase gene, or a fragment thereof. In other embodiments, a cured tobacco is made from a hybrid, variety, or line comprising plants transformed with an RNAi construct comprising a nucleic acid sequence selected from the group consisting of SEQ ID NO:5, SEQ ID NO:6, SEQ ID NO:7, and SEQ ID NO:8. In certain embodiments, cured tobacco material is made by a curing process selected from the group consisting of flue curing, air curing, fire curing and sun curing.

Also provided herein are tobacco products. In one particular embodiment, a tobacco product comprises cured tobacco material obtained from a hybrid, variety, or line comprising plants having a mutant allele at a nicotine demethylase locus. In other embodiments, a cured tobacco is made from a hybrid, variety, or line comprising plants transformed with an RNAi construct comprising a nicotine demethylase gene, or a fragment thereof. In other embodiments, a cured tobacco is made from a hybrid, variety, or line comprising plants transformed with an RNAi construct comprising a nucleic acid sequence selected from the group consisting of SEQ ID NO:5, SEQ ID NO:6, SEQ ID NO:7, and SEQ ID NO:8. In certain embodiments, a tobacco product is a cigarette product, a cigar product, a pipe tobacco product, a smokeless tobacco product, a film, a tab, a gel, a shaped part, a rod, or a foam.

Provided herein are M1 tobacco plants and progeny of $M_1$ tobacco plants. An $M_1$ tobacco plant can be heterozygous for a mutant allele at a nicotine demethylase locus and produce progeny, wherein at least a portion of first generation self-pollinated progeny of said plant exhibit a non-converter phenotype. Progeny of said $M_1$ tobacco plant can revert to a converter phenotype at a rate that is statistically significantly less than the reversion rate of the progeny of the corresponding tobacco plant that comprises a wild type allele at said nicotine demethylase locus. An $M_1$ tobacco plant can exhibit a non-converter phenotype and produce progeny that can revert to a converter phenotype at a rate that is statistically significantly less than the reversion rate of the progeny of a corresponding tobacco plant that comprises a wild type allele at said nicotine demethylase locus. In one particular embodiment, a plant or progeny is essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TN 86, TN86LC, TN 90, TN 97, TN97LC, TN D94, TN D950, TR (Tom Rosson) Madole, VA 309, or VA359.

Also provided herein are tobacco hybrids, varieties, or lines, where plants of the hybrids, varieties, or lines are transformed with an RNAi construct comprising a nicotine demethylase gene, or a fragment thereof, and where the plants exhibit decreased expression of a nicotine demethylase gene as compared to plants of a control tobacco hybrid, variety, or line lacking the RNAi construct. The nicotine demethylase gene, or a fragment thereof, can be from 25 to 500 or from 100 to 300 nucleotides in length. A tobacco hybrid, variety, or line can be a Burley type, a dark type, a flue-cured type, or an Oriental type tobacco. A tobacco hybrid, variety, or line can be a *Nicotiana tabacum* hybrid, variety, or line. A variety can be essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359. A hybrid, variety, or line can be a *Nicotiana tabacum* hybrid, variety, or line.

Also provided herein are tobacco hybrids, varieties, or lines, where plants of said hybrid, variety, or line are transformed with an RNAi construct comprising a nucleic acid sequence selected from the group consisting of SEQ ID NO:5, SEQ ID NO:6, SEQ ID NO:7, and SEQ ID NO:8, and where the plants exhibit decreased expression of a nicotine demethylase gene as compared to plants of a control tobacco hybrid, variety, or line lacking the RNAi construct. A variety can be essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, CL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC3, NC4, NC5, NC6, NC7, NC606, NC71, NC72, NC810, NC BH129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359.

Provided herein are methods of making a tobacco plant. The methods comprise introducing into a cell of a *Nicotiana* plant an RNAi construct comprising a nicotine demethylase gene, or a fragment thereof, obtaining one or more plants from said cell, identifying at least one of the plants that exhibits decreased expression of a nicotine demethylase gene as compared to the corresponding tobacco plant lacking RNAi construct. The methods can further comprise crossing a plant containing the RNAi construct with a second *Nicotiana* plant, and selecting progeny of the cross exhibiting decreased expression of a nicotine demethylase gene as compared to the corresponding tobacco plant lacking the RNAi construct.

In certain other embodiments, the invention is directed to methods of making a tobacco plant. In particular embodiments, a method of making a tobacco plant comprises crossing a plant containing transformed with an RNAi construct comprising a nicotine demethylase gene, or a fragment thereof, with a second *Nicotiana* plant; and selecting progeny of the cross that have the RNAi construct.

In some embodiments, the second tobacco plant exhibits a phenotypic trait such as disease resistance; high yield; high grade index; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves). In still other embodiments, the method further includes self-pollinating or pollinating a male sterile pollen acceptor with a pollen donor capable of being used in production of a hybrid or a male sterile hybrid. Either the male sterile pollen acceptor plant or the pollen donor plant is transformed with an RNAi construct comprising a nicotine demethylase gene, or a fragment thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the detailed description set forth below. Other features, objects, and advantages of the invention will be apparent from the description and drawings, and from the claims.

DESCRIPTION OF THE DRAWINGS

FIG. 1 depicts percent conversion of nicotine to nornicotine as measured by gas chromatography in ethylene-treated leaves of TN90 tobacco lines relative to mutation status. A: Line 4246, B: Line 1849, C: Line 4278, D: Line 4215, E: Line 3320, and F: Line 1394. "Hetero" indicates the plant is heterozygous for a mutant nicotine demethylase allele. "Homo" indicates the plant is homozygous for a mutant nicotine demethylase allele. "Wild" indicates the plant is homozygous for wild-type nicotine demethylase.

FIG. 2 shows a nicotine demethylase nucleic acid sequence (SEQ ID NO:1) and amino acid sequence (SEQ ID NO:2). Numbers corresponding to the nucleotide sequence are on the left side and numbers corresponding to the amino acid sequence are on the right side. The Web Signal Scan program and sequence alignment tools were used to identify the following: substrate recognition sites (boxed), N-terminal hydrophobic transmembrane domain (underlined), proline-rich region (underlined and in italics), threonine-containing oxygen-binding pocket (dotted underlined), K-helix and PERF consensus (dashed underlined), and cysteine-containing heme-binding region (double underlined and in bold).

DETAILED DESCRIPTION

Figure 3:
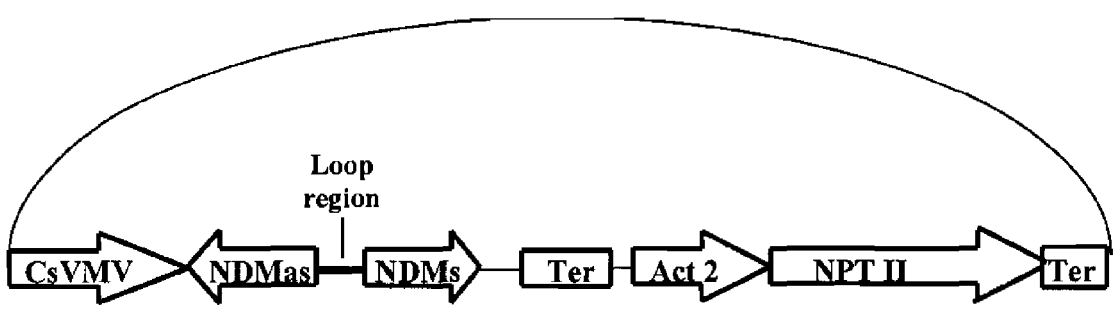
FIG. 3 shows a schematic of a nicotine demethylase RNAi construct. CsVMV-Cassava vein mosaic virus promoter; NDMas-antisense nicotine demethylase sequence; NDMs-sense nicotine demethylase sequence; Ter-Nos terminator; Act2-*Arabidopsis thaliana* Actin 2 promoter; NPTII-neomycin phosphotransferase II gene.

The present invention is directed to compositions and methods related to tobacco plants having reduced nicotine demethylase activity. For example, this document provides tobacco plants comprising one or more mutations in a nicotine demethylase gene. This document also provides tobacco plants comprising a double-stranded RNA comprising a nucleic acid sequence from a nicotine demethylase gene. Such tobacco plants comprising a mutant nicotine demethylase sequence in its genome or a double-stranded RNA comprising a nucleic acid sequence from a nicotine demethylase gene typically have a reduced nornicotine content. Such plants are useful in tobacco breeding programs, in making cured tobacco and in making various tobacco products and/or tobacco derived products.

Mutations in a Nicotine Demethylase Gene

Tobacco plants described herein are typically generated by inducing mutagenesis in cells of a *Nicotiana* species. The term "mutagenesis" refers to the use of a mutagenic agent to induce genetic mutations within a population of individuals. A population to be mutagenized can comprise plants, parts of plants, or seeds. For mutagenized populations the dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based upon the expected frequency of mutations.

The mutagenized population, or a subsequent generation of that population, is then screened for a desired trait(s) (e.g., a non-converter phenotype) that results from the mutation(s). Alternatively, the mutagenized population, or a subsequent generation of that population, is screened for a mutation in a gene of interest, e.g., a nicotine demethylase gene. For example, the progeny $M_2$ generation of $M_1$ plants may be evaluated for the presence of a mutation in a nicotine demethylase gene. A "population" is any group of individuals that share a common gene pool. As used herein, "$M_0$" refers to plant cells(and plants grown therefrom) exposed to a mutagenic agent, while "$M_1$" refers to seeds produced by self-pollinated $M_0$ plants, and plants grown from such seeds. "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

Suitable mutagenic agents include, for example, chemical mutagens and ionizing radiation. Chemical mutagens suitable for inducing mutations include nitrous acid, sodium azide, acridine orange, ethidium bromide and ethyl methane sulfonate. Ionizing radiation suitable for inducing mutations includes X-rays, gamma rays, fast neutron irradiation and UV radiation. Other methods include the use of transposons (Fedoroff et al., 1984; U.S. Pat. No. 4,732,856 and U.S. Pat. No. 5,013,658), as well as T-DNA insertion methodologies (Hoekema et al., 1983; U.S. Pat. No. 5,149,645). The types of mutations that may be induced in a tobacco gene include, for example, point mutations, deletions, insertions, duplications, and inversions.

In some embodiments, mutagenesis is induced by growing plant cells in tissue culture, which results in the production of somaclonal variants. Alternatively, application of standard protoplast culture methodologies developed for production of hybrid plants using protoplast fusion is also useful for generating plants having variant gene expression (e.g., variant nicotine demethylase gene expression). Accordingly, protoplasts are generated from a first and a second tobacco plant having variant gene expression. Calli are cultured from successful protoplast fusions and plants are then regenerated. Resulting progeny hybrid plants are identified and selected for variant gene expression according to methods described herein and may be used in a breeding protocols described herein.

The term "nicotine demethylase gene" as used herein refers to a genomic nucleic acid sequence encoding a nicotine demethylase polypeptide. A nicotine demethylase gene includes coding sequences at a nicotine demethylase locus, as well as noncoding sequences such as regulatory regions, introns, and other untranslated sequences. A wild-type nicotine demethylase gene can comprise the nucleic acid sequence set forth in SEQ ID NO:1. A wild-type CYP82E5 nicotine demethylase gene can comprise the coding sequence set forth in SEQ ID NO:12. The term "nicotine demethylase polypeptide" as used herein refers to a cytochrome P450 CYP82E4 or CYP82E5 polypeptide having nicotine demethylase activity. "Nicotine demethylase activity" is the ability to N'-demethylate nicotine to produce nornicotine. A wild-type CYP82E4 nicotine demethylase polypeptide can comprise the amino acid sequence set forth in SEQ ID NO:2. A wild-type CYP82E5 nicotine demethylase polypeptide can comprise the amino acid sequence set forth in SEQ ID NO:13.

As provided herein (e.g., in FIG. 2 and Example 5), a nicotine demethylase polypeptide can contain regions having homology with conserved domains in other cytochrome P450 polypeptides. For example, a polypeptide having the sequence set forth in SEQ ID NO:2 contains six substrate recognition sites (SRS), an N-terminal hydrophobic transmembrane domain, a proline-rich region, a threonine-containing oxygen-binding pocket, a K-helix consensus, a PERF consensus, and a cysteine-containing heme-binding region, as identified by the TFSEARCH and Web Signal Scan programs. See FIG. 2. The K-helix and PERF consensus sequences are thought to stabilize the core structure of cytochrome P450 polypeptides. The heme-binding region contains a cysteine that is absolutely conserved in electron donor-dependent cytochrome P450 polypeptides. The proline-rich region is thought to form a hinge between the transmembrane region and the globular part of the polypeptide. See, e.g., Werck-Reichhart and Feyereisen (2000) *Genome Biology* 1:3003.

Preferably, a mutation in a nicotine demethylase gene results in reduced or even complete elimination of nicotine demethylase activity in a plant comprising the mutation. Suitable types of mutations in a nicotine demethylase gene include, without limitation, insertions of nucleotides, deletions of nucleotides, or transitions or transversions in the wild-type nicotine demethylase gene sequence. Mutations in the coding sequence can result in insertions of one or more amino acids, deletions of one or more amino acids, and/or non-conservative amino acid substitutions in the corresponding gene product. In some cases, the sequence of a nicotine demethylase gene comprises more than one mutation or more than one type of mutation.

Insertion or deletion of amino acids in a coding sequence can, for example, disrupt the conformation of a substrate binding pocket of the resulting gene product. Amino acid insertions or deletions can also disrupt catalytic sites important for gene product activity (e.g., a heme-binding site). It is known in the art that the insertion or deletion of a larger number of contiguous amino acids is more likely to render the gene product non-functional, compared to a smaller number of inserted or deleted amino acids. Examples of such mutations are mutations in a CYP82E4 nicotine demethylase gene encoding the amino acid sequence set forth in SEQ ID NO:2, which result in the tryptophan at amino acid 229 or at 239 being replaced with a stop codon. The resulting mutant polypeptides are thereby truncated. Other examples of such mutations are mutations in a CYP82E5 nicotine demethylase gene encoding the amino acid sequence set forth in SEQ ID NO:13, which result in the tryptophan at amino acid 229 or at 329 being replaced with a stop codon, and a truncated polypeptide. A mutation in a CYP82E5 gene encoding the amino acid sequence set forth in SEQ ID NO:13 can include a mutation that replaces any of amino acids 1-328 with a stop codon.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for a isoleucine residue. Examples of non-conservative substitutions include a basic amino acid for a non-polar amino acid, or a polar amino acid for an acidic amino acid. An example of such mutations is a mutation in a nicotine demethylase gene encoding the amino acid sequence set forth in SEQ ID NO:2, which mutation results in the proline at amino acid 107 being replaced by a leucine.

In some embodiments, a mutation in a nicotine demethylase gene results in no amino acid changes (e.g., a silent mutation). Silent mutations are mutations in a nucleotide sequence that do not affect the amino acid sequence of the encoded polypeptide. Silent mutations effective for reducing nicotine demethylase activity include mutations in the nicotine demethylase gene of SEQ ID NO:1, in which the guanine at nucleic acid +2021 is replaced with an adenine, or the guanine at nucleic acid +2291 is replaced with an adenine. Other mutations that result in no amino acid changes can be in a 5' noncoding region (e.g., a promoter or a 5' untranslated region), an intron, or a 3' noncoding region. Such mutations, although not affecting the amino acid sequence of the encoded nicotine demethylase, may alter transcriptional levels (e.g., increasing or decreasing transcription), decrease translational levels, alter secondary structure of DNA or mRNA, alter binding sites for transcriptional or translational machinery, or decrease tRNA binding efficiency. Suitable mutations that reduce or eliminate nicotine demethylase activity include mutations that insert a splice donor in the intron of the nicotine demethylase gene, insert a splice acceptor in the intron, or delete a splice site of the intron.

In certain embodiments, a mutation in a nicotine demethylase gene effective for reducing nicotine demethylase activity is determined by identifying a plant having a mutation in a nicotine demethylase gene and measuring nicotine demethylase enzyme activity. In other embodiments, a mutation in a nicotine demethylase gene that is suitable for reducing nicotine demethylase activity is predicted based on the effect of mutations described herein, e.g., those mutations contained in TN90 lines 4246, 1849, 4278, and 4215 as set forth in Table 1 and Table 3. For example, a mutation in a nicotine demethylase gene encoding the amino acid sequence set forth in SEQ ID NO:2 can include a mutation that replaces any of amino acids 1-328 with a stop codon. In other embodiments, a mutation in a nicotine demethylase gene that is effective for reducing nicotine demethylase activity is identified based on the effect of a similar mutation in a related sequence. For example, a CYP82E4 nicotine demethylase gene can be mutated such that it encodes a mutation identified in a CYP82E5 gene, and vice versa.

In another embodiment, a mutation in a nicotine demethylase gene that is effective for reducing nicotine demethylase activity is identified based on the function of related sequences, e.g., SEQ ID NO:3 and SEQ ID NO:4. For example, a nicotine demethylase gene can be mutated such that it encodes a nicotine demethylase polypeptide having a combination of mutations in SEQ ID NO:2, such as the combination of I163M, K309E, G353C, and S452P, or the combination of Q416L and S423P.

In certain other embodiments, a mutation in a nicotine demethylase gene that is effective for reducing nicotine demethylase activity is identified based on a molecular model or sequence analysis of the structure of a nicotine demethylase polypeptide. Such a molecular model or sequence analysis can be used to identify which amino acids, when mutated, will change the structure or function of the polypeptide. For example, a molecular model can be used to identify which amino acids in a substrate binding pocket can be deleted or substituted with a nonconservative amino acid to reduce the level of conversion of nicotine to nornicotine. In another example, sequence analysis can determine which amino acids can be replaced with a stop codon to disrupt a conserved domain. For example, a mutation in a CYP82E4 nicotine demethylase gene encoding the amino acid sequence set forth in SEQ ID NO:2 can include a mutation that replaces any of amino acids 330-457 with a stop codon, thereby disrupting the heme-binding site of nicotine demethylase. Similarly, a mutation in a CYP82E5 gene encoding the amino acid sequence set forth in SEQ ID NO:13 can include a mutation that replaces any of amino acids 330-458 with a stop codon.

Tobacco Plants Having Mutant Nicotine Demethylase Alleles

One or more $M_1$ tobacco plants are obtained from cells of mutagenized individuals and at least one of the plants is identified as containing a mutation in a nicotine demethylase gene. An $M_1$ tobacco plant may be heterozygous for a mutant allele at a nicotine demethylase locus and, due to the presence of the wild-type allele, exhibit a converter phenotype, i.e., be capable of converting nicotine to nornicotine. In such cases, at least a portion of first generation self-pollinated progeny of such a plant exhibit a non-converter phenotype. Alternatively, an $M_1$ tobacco plant may have a mutant allele at a nicotine demethylase locus and exhibit a non-converter phenotype. Such plants may be heterozygous and exhibit a non-converter phenotype due to phenomena such a dominant negative suppression, despite the presence of the wild-type allele, or may be homozygous due to independently induced mutations in both alleles at the nicotine demethylase locus. Subsequent progeny of both types of $M_1$ plants, however, revert to a converter phenotype at a rate that is statistically significantly less than the reversion rate of the progeny of a corresponding tobacco plant that is wild type at the nicotine demethylase locus, as discussed below.

$M_1$ tobacco plants carrying mutant nicotine demethylase alleles can be from Nicotiana species such as Nicotiana tabacum, Nicotiana otophora, Nicotiana thrysiflora, Nicotiana tomentosa, Nicotiana tomentosiformis, Nicotiana africana, Nicotiana amplexicaulis, Nicotiana arentsii, Nicotiana benthamiana, Nicotiana bigelovii, Nicotiana corymbosa, Nicotiana debneyi, Nicotiana excelsior, Nicotiana exigua, Nicotiana glutinosa, Nicotiana goodspeedii, Nicotiana gossei, Nicotiana hesperis, Nicotiana ingulba, Nicotiana knightiana, Nicotiana maritima, Nicotiana megalosiphon, Nicotiana miersii, Nicotiana nesophila, Nicotiana noctiflora, Nicotiana nudicaulis, Nicotiana otophora, Nicotiana palmeri, Nicotiana paniculata, Nicotiana petunioides, Nicotiana plumbaginifolia, Nicotiana repanda, Nicotiana rosulata, Nicotiana rotundifolia, Nicotiana rustica, Nicotiana setchelli, Nicotiana stocktonii, Nicotiana eastii, Nicotiana suaveolens or Nicotiana trigonophylla.

Particularly useful Nicotiana tabacum varieties include Burley type, dark type, flue-cured type, and Oriental type tobaccos, such as tobacco varieties BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, DT 538 LC, Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT200LC, KT204LC, KT206LC, KT D4 LC, KT D6 LC, KT D8LC, KY 10, KY 14, KY 160, KY 17, KY 171, KY 907, KY907LC, KTY14 x L8 LC, Little Crittenden, McNair 373, McNair 944, msKY 14xL8, N-126, N-777LC, N-7371LC, Narrow Leaf Madole, Narrow Leaf Madole LC, NBH 98, NC 100, NC 102, NC 2000, NC 291, NC 297, NC 299, NC 3, NC 4, NC 5, NC 6, NC7, NC 606, NC 71, NC 72, NC 810, NC BH 129, NC BH 129 LC, NC 2002, Neal Smith Madole, OXFORD 207, PD 7302 LC, PD 7309 LC, PD 7312 LC, 'Perique' tobacco, PVH03, PVH09, PVH19, PVH50 PVH51, PVH 1118, R 610, R 610-LC, R 630, R 630LC, R 7-11, R 7-12, R 7-12LC, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 90LC, TN 97, TN97LC, TN D94, TN D950, TR (Tom Rosson) Madole, VA 309, or VA359.

A tobacco plant carrying a mutant nicotine demethylase allele can be used in a plant breeding program to create novel and useful lines, varieties and hybrids. Thus, in some embodiments, an $M_1$, $M_2$, $M_3$, or later generation tobacco plant containing at least one mutation in a nicotine demethylase gene is crossed with a second Nicotiana plant, and progeny of the cross are identified in which the nicotine demethylase gene mutation(s) is present. It will be appreciated that the second Nicotiana plant can be one of the species and varieties described herein. It will also be appreciated that the second Nicotiana plant can contain the same nicotine demethylase mutation as the plant to which it is crossed, a different nicotine demethylase mutation, or be wild-type at the nicotine demethylase locus.

Breeding is carried out via known procedures. DNA fingerprinting, SNP or similar technologies may be used in a marker-assisted selection (MAS) breeding program to transfer or breed mutant alleles of a nicotine demethylase gene into other tobaccos, as described herein. For example, a breeder can create segregating populations from hybridizations of a genotype containing a mutant allele with an agronomically desirable genotype. Plants in the $F_2$ or backcross generations can be screened using a marker developed from a nicotine demethylase sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

*Nicotiana* species which exhibit breeding compatibility with *Nicotiana tabacum* include *Nicotiana amplexicaulis*, PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc.

Successful crosses yield $F_1$ plants that are fertile and that can be backcrossed with one of the parents if desired. In some embodiments, a plant population in the $F_2$ generation is screened for variant nicotine demethylase gene expression, e.g., a plant is identified that fails to express nicotine demethylase due to the absence of a nicotine demethylase gene according to standard methods, for example, by using a PCR method with primers based upon the nucleotide sequence information for nicotine demethylase described herein. Selected plants are then crossed with one of the parents and the first backcross ($BC_1$) generation plants are self-pollinated to produce a $BC_1F_2$ population that is again screened for variant nicotine demethylase gene expression (e.g., the null version of the nicotine demethylase gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant nicotine demethylase gene expression (e.g., a plant that displays the null condition for nicotine demethylase) or variant expression of NDM nucleic acid sequence, or a fragment thereof. Cytogenetic analyses of the selected plants are optionally performed to confirm the chromosome complement and chromosome pairing relationships. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nornicotine to nicotine+nornicotine.

In situations where the original $F_1$ hybrid resulting from the cross between a first, mutant tobacco parent (e.g., TN 90) and a second, wild-type tobacco parent (e.g., *N. rustica*), is hybridized or backcrossed to the mutant tobacco parent, the progeny of the backcross can be self-pollinated to create a $BC_1F_2$ generation that is screened for the mutant nicotine demethylase allele.

The result of a plant breeding program using the mutant tobacco plants described herein are novel and useful lines, hybrids and varieties. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A "line" as distinguished from a variety most often denotes a group of plants used non-commercially, for example in plant research. A line typically displays little overall variation between individuals for one or more traits of interest, although there may be some variation between individuals for other traits.

Of particular interest are CYP82E4 and CYP82E5 double mutant tobacco plants. Tobacco plants homozygous for mutations in both CYP82E4 and CYP82E5 have a reversion rate that is statistically significantly lower than corresponding control low-converter plants having wild type nicotine demethylase CYP82E4 and E5 genes. In addition, homozygous CYP82E4 and CYP82E5 double mutant tobacco plants have a percent conversion to nornicotine of less than 2.0%, e.g., undetectable to 2.0%, undetectable to 0.3%, 0.1 to 0.5%, 0.1 to 1.0%, 0.1 to 0.8%, 0.3 to 0.8%, 0.5 to 1.0%, 0.5 to 2.0%, 0.7 to 1.5%, 0.8 to 1.8%, 0.8 to 2.0%, or 1.0 to 2.0%. The percent conversion for homozygous double mutant plants can be similar to or lower than that observed in tobacco plants containing transgenes that induce RNAi-induced downregulation of nicotine demethylase.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting $F_1$ seed is harvested.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

As used herein, a tobacco plant having a converter phenotype is a tobacco plant having a percent nicotine demethylation of at least 5% (e.g., 5.0%, 5.1%, 5.5%, 6%, 8%, 15%, 30%, 50%, 70%, 90%, 95%, 98%, or 99%) as measured in an ethylene-treated middle position leaf harvested from a tobacco plant at knee-high stage or later. The terms "plant having a converter phenotype" and "converter plant" are used interchangeably herein. Similarly, a tobacco plant having a non-converter phenotype is a tobacco plant having a percent nicotine demethylation of less than 5% (e.g., 4.9%, 4.5%, 4.2%, 4%, 3.8%, 3.5%, 3%, 2%, 1%, 0.8%, 0.6%, 0.5%, 0.05%, 0.02%, 0.01%, or undetectable) as measured in an ethylene-treated middle position leaf harvested from a tobacco plant at knee-high stage or later. The terms "plant having a non-converter phenotype" and "non-converter plant" are used interchangeably herein.

Nicotine and nornicotine can be measured in ethylene-treated leaves using methods known in the art (e.g., gas chromatography). Percent nicotine demethylation in a sample is calculated by dividing the level of nornicotine by the combined level of nicotine and nornicotine as measured in the sample, and multiplying by 100.

A plant comprising a mutation in a nicotine demethylase gene can be identified by selecting or screening the mutagenized plant material, or progeny thereof Such screening and selection methodologies are known to those having ordinary skill in the art. Examples of screening and selection methodologies include, but are not limited to, Southern analysis, or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

A population of plants can be screened and/or selected for those members of the population that have a desired trait or phenotype conferred by a mutation in a nicotine demethylase gene, such as a non-converter phenotype. Selection and/or screening can be carried out over one or more generations, which can be useful to identify those plants that have a desired trait. In some embodiments, plants having a non-converter phenotype can be identified in the $M_1$ generation. Selection and/or screening can also be carried out in more than one geographic location. In addition, selection and/or screening can be carried out during a particular developmental stage in which the phenotype is exhibited by the plant.

A population of plants having a non-converter phenotype can be used to select and/or screen for plants with a reduced reversion rate, i.e., the percentage of converter phenotype plants in the next generation progeny of a non-converter plant. Reversion rate is measured by collecting seeds produced by a non-converter plant after self-pollination, planting 300 to 500 of the seeds, and determining the number of resulting plants having a converter phenotype. The reversion rate is expressed as the percentage of progeny plants that have a converter phenotype.

A non-converter plant having a mutation in a nicotine demethylase gene and exhibiting a reduced reversion rate can be bred to generate one or more tobacco hybrids, varieties or lines having a reversion rate that is statistically significantly less than the reversion rate of a control tobacco hybrid, variety or line having the same or similar genetic background, but carrying a wild type nicotine demethylase gene. Typically, a reduction in the reversion rate relative to a control hybrid, variety or line is considered statistically significant at $p \leq 0.05$ with an appropriate parametric or non-parametric statistic, e.g., Chi-square test, Student's t-test, Mann-Whitney test, or F-test. In some embodiments, a reduction in the reversion rate is statistically significant at $p<0.01$, $p<0.005$, or $p<0.001$.

The extent to which reversion rate is reduced typically depends on the tobacco type. For example, a non-converter Burley type tobacco having a mutation in a nicotine demethylase gene typically has a reversion rate that is reduced 10× or more (e.g., 10× to 1000×, 10× to 100×, 50× to 250×, 50× to 100×, 150× to 300×, 100× to 1000×, 500× to 1000×, 800× to 5000×, or 1500× to 10000×) relative to a Burley type tobacco variety of the same or similar genetic background, but having a wild type nicotine demethylase gene. In another example, a non-converter dark type tobacco having a mutation in a nicotine demethylase gene typically has a reversion rate that is reduced 2× or more (e.g., 2× to 100×, 2× to 5×, 2× to 10×, 5× to 30×, 10× to 50×, 5× to 100×, 10× to 100×, 50× to 300×, 250× to 500×, 300× to 3000×, or 3000× to 5000×) relative to a dark type tobacco variety of the same or similar genetic background, but having a wild type nicotine demethylase gene. In another example, a non-converter flue-cured type tobacco having a mutation in a nicotine demethylase gene typically has a reversion rate that is reduced 2× or more (e.g., 2× to 10×, 5× to 30×, 10× to 50×, 10× to 100×, 50× to 150×, 100× to 500×, 200× to 800×, 400× to 1000×, 500× to 3000×, to 1000× to 5000×) relative to a flue-cured type tobacco variety of the same or similar genetic background, but having a wild type nicotine demethylase gene. In some cases, the reversion rate of tobacco hybrids, varieties or lines comprising plants having a mutation in a nicotine demethylase gene can be so low as to be undetectable.

The method of screening for reduced reversion rate can depend on the source of the mutagenized plant material. For example, if the mutagenized plant material is seed from a plant having a converter phenotype, suitable methods of screening include identifying progeny having a mutation in a nicotine demethylase gene and/or identifying progeny having a non-converter phenotype. Once such progeny are identified, they are screened for those plants whose progeny exhibit a reduced reversion rate. In another example, if the mutagenized plant material is seed from a plant having a non-converter phenotype, a suitable method of screening includes identifying progeny having a mutation in a nicotine demethylase gene and/or determining whether progeny have a reduced reversion rate.

In some embodiments of methods described herein, lines resulting from breeding and screening for variant nicotine demethylase genes are evaluated in the field using standard field procedures. Control genotypes including the original unmutagenized parent are included and entries are arranged in the field in a randomized complete block design or other appropriate field design. Standard agronomic practices for tobacco are used, for example, the tobacco is harvested, weighed, and sampled for chemical and other common testing before and during curing. Statistical analyses of the data are performed to confirm the similarity of the selected lines to the parental line.

Nicotine Demethylase RNA Interference

Transformation vectors suitable for RNA interference (RNAi) include those that produce RNAs capable of duplex formation (e.g., a nicotine demethylase RNAi construct), two nucleic acid sequences, one in the sense and the other in the antisense orientation, may be operably linked, and placed under the control of a promoter, such as CAMV 35S, the promoter isolated from cassava brown streak virus (CBSV), or the promoter isolated from cassava vein mosaic virus (Cs-VMV). Use of an endogenous promoter, such as a nicotine demethylase promoter, or a fragment thereof that drives transcription, may also be desirable. In addition, such a nucleic acid can be operably linked to a transcription terminator sequence, such as the terminator of the nopaline synthase (nos) gene.

The length of tobacco nicotine demethylase nucleic acid sequences included in such a construct is desirably at least 22 nucleotides, e.g., at least 22, 23, 24, 25, 26, 27, 30, 35, 40, 50, 80, 100, 200, 300, 400, 500, 700, 1000, 2000 nucleotides or more, but may encompass a sequence that includes up to a full-length tobacco nicotine demethylase gene. The length of tobacco nicotine demethylase nucleic acid sequences included in such a construct can be from 22 nucleotides to 2552 nucleotides, e.g., 22 to 100 nucleotides, 25 to 250 nucleotides, 25 to 500 nucleotides, 50 to 100 nucleotides, 50 to 500 nucleotides, 100 to 300 nucleotides, 100 to 500 nucleotides, 300 to 600 nucleotides, 500 to 1000 nucleotides, 700 to 1500 nucleotides, or 1000 to 2000 nucleotides. Generally, higher homology can be used to compensate for the use of a shorter sequence. Suitable nucleic acids for use in a nucleic acid construct encoding a double-stranded RNA that are similar or identical to a nicotine demethylase gene include SEQ ID NO:5, SEQ ID NO:6, SEQ ID NO:7, and SEQ ID NO:8, and complements thereof.

An RNA capable of duplex formation can comprise a loop portion. The loop portion of a double-stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. Suitable loop portions include SEQ ID NO:9, SEQ ID NO:10, and SEQ ID NO:11.

Utility

Mutant and transgenic tobacco plants provided herein have particular uses in agricultural industries. Such a plant can be used in a breeding program as described herein to produce a tobacco line, variety or hybrid comprising plants having a non-converter phenotype, wherein the line, variety or hybrid has a reduced reversion rate as compared to a corresponding tobacco line, variety or hybrid that is wild type for the nicotine demethylase gene or lacks a nicotine demethylase RNAi construct. In some cases, the mutant or transgenic tobacco plants provided herein can be crossed to plants having another desired trait to produce tobacco varieties having both a reduced reversion rate and another desired trait. Examples of other desired traits include drought tolerance, disease resistance, nicotine content, sugar content, leaf size, leaf width, leaf length, leaf color, leaf reddening, internode length, flowering time, lodging resistance, stalk thickness, leaf yield, disease resistance; high yield; high grade index; curability; curing quality; mechanical harvestability; holding ability; leaf quality; height; maturation; stalk size; and leaf number per plant. Tobacco lines, varieties or hybrids can be bred according to standard procedures in the art.

In other cases, based on the effect of disclosed nicotine demethylase mutations on the phenotype of plants having such mutations, one can search for and identify tobacco plants carrying in their genomes naturally occurring mutant alleles in a nicotine demethylase locus. Such plants can be used in a breeding program to produce a tobacco line, variety or hybrid comprising plants having a mutation in a nicotine demethylase gene, such a line, variety or hybrid having a reduced reversion rate as compared to a corresponding tobacco line, variety or hybrid having a wild type nicotine demethylase gene.

In certain embodiments, tobacco lines, varieties or hybrids comprising plants having a mutation in a nicotine demethylase gene or comprising a nicotine demethylase RNAi construct provided herein are used to produce tobacco material for use in making tobacco products. Suitable tobacco material includes whole leaf, tobacco fines, tobacco dust, sized tobacco lamina, cut or roll pressed tobacco stem, volume expanded tobacco and shredded tobacco. Tobacco material from the disclosed mutant tobacco plants can be cured using curing methods known in the art such as air curing, fire curing, flue curing (e.g., bulk curing), and sun curing. In some embodiments, tobacco material is conditioned and/or fermented. See, e.g., U.S. Patent Publication No. 2005/0178398.

In other embodiments, tobacco lines, varieties or hybrids comprising plants having a mutation in a nicotine demethylase gene or comprising a nicotine demethylase RNAi construct provided herein are used to make a tobacco product having a reduced nornicotine content as compared to a corresponding product comprising tobacco obtained from a corresponding tobacco line, variety or hybrid comprising plants comprising a wild type nicotine demethylase gene. Tobacco products having a reduced amount of nitrosamine content can be manufactured using tobacco plant material described herein. The tobacco product typically has a reduced amount of nornicotine of less than about 5 mg/g. For example, the nornicotine content in such a product can be 4.5 mg/g, 4.0 mg/g, 3.5 mg/g, 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 7.0 µg/g, 5.0 µg/g, 4.0 µg/g, 2.0 µg/g, 1.0 µg/g, 0.5 µg/g, 0.4 µg/g, 0.2 µg/g, 0.1 µg/g, 0.05 µg/g, 0.01 µg/g, or undetctable. The tobacco product typically has a reduced amount of NNN of less than about 50 µg/g. For example, the nornicotine content in such a product can be 40 µg/g, 25 µg/g, 10 µg/g, 7.0 µg/g, 5.0 µg/g, 4.0 µg/g, 2.0 µg/g, 1.0 µg/g, 0.5 µg/g, 0.4 µg/g, 0.2 µg/g, 0.1 µg/g, 0.05 µg/g, 0.01 µg/g, or undetectable. The percentage of secondary alkaloids relative to total alkaloid content contained therein is less than 90%, e.g., less than 70%, 50%, 30%, 10%, 5%, 4%, 3%, 2%, 1.5%, 1%, 0.75%, 0.5%, 0.25%, or 0.1%.

The phrase "a reduced amount" with respect to nomicotine or NNN refers to an amount of nomicotine or NNN or both in a tobacco plant or plant component or a tobacco product that is less than what would be found in a wild-type tobacco plant or plant component or tobacco product from the same variety of tobacco, processed in the same manner, which was not made transgenic for reduced nomicotine or NNN or does not have a mutation in a nicotine demethylase gene. In one example, a wild-type tobacco plant of the same variety that has been processed in the same manner is used as a control to measure whether a reduction of nomicotine or NNN or both has been obtained by the methods described herein. In another example, plants having a reduced amount of nitrosamine content are evaluated using standard methods, for instance, by monitoring the presence or absence of a gene or gene product, e.g., a nicotine demethylase, a transgene, or a particular mutation in a gene. In still another example, nitrosamine content of plants resulting from a breeding program are compared to the nitrosamine content of one of the parent lines used to breed the plant having the reduced amount of nitrosamine. Levels of nornicotine and NNN or both are measured according to methods well known in the tobacco art.

In certain embodiments tobacco material obtained from the tobacco lines, varieties or hybrids provided herein is used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548.

The invention will be further described in the following examples, which do not limit the scope of the invention described in the claims.

EXAMPLES

Example 1

Production of Mutant *Nicotiana* Plants

One gram of tobacco TN90 (Tennessee 90) converter seed (approximately 10,000 seeds) was washed in 0.1% Tween® for fifteen minutes and then soaked in 30 ml of ddH$_2$O for two hours. One hundred fifty (150) µl (0.5%) of EMS (Sigma Catalogue No. M-0880) was then mixed into the seed/ddH$_2$O solution and incubated for 8-12 hours (rotating at 30 rpm) under a hood at room temperature (RT, approximately 20° C.). The liquid was then removed from the seeds and the liquid was mixed into 1 M NaOH overnight for decontamination and disposal. The seeds were then washed twice with 100 ml ddH$_2$O for 2-4 hours. The washed seeds were then suspended in 0.1% agar:water solution.

The EMS treated seeds in agar solution were evenly spread onto water soaked Carolina's Choice Tobacco Mix™ (Carolina Soil Company, Kinston, N.C.) in flats at a rate of ~2000 seeds/flat. The flats were then covered by Saran™ wrap and placed in a growth chamber. Once the seedlings emerged from the soil, the Saran™ wrap was punctured to allow humidity to decline gradually. The Saran™ wrap was removed completely after two weeks. Flats were moved to a greenhouse and fertilized with NPK fertilizer. The seedlings were plugged into a float tray and grown until transplanting size. The plants were transplanted into a field. During growth, the plants were self-pollinated to form $M_1$ seeds. At the mature stage, five capsules were harvested from each of around 7000 plants and individual designations were given to the set of seeds from each plant. This formed the $M_1$ population.

Example 2

Identification of Mutations

A composite of $M_1$ seed from each $M_0$ plant of Example 1 was grown, leaves from 4 to 5 $M_1$ plants were pooled and DNA was extracted from the pooled tissue samples. Two pooled samples were taken from each $M_1$ line. DNeasy plant mini kits (QIAGEN, Catalogue no. 69104) were used for DNA extraction, following the manufacturer's manual.

IRDye™ 700-labeled forward primers and RDye™ 800-labeled reverse primers were designed to amplify a nicotine demethylase gene (SEQ ID NO:1). Two pairs of sequence specific primers, which covered two separate exons, were selected to amplify the nicotine demethylase (ND) gene by PCR. Primers F6 (5'-GGAATTATGCCCATCCTACAG) and R1 (5'-CCAGCATTGCAGGGTTCGGGAAGA) covered the ND gene from −82 to +1139 and generated a 1,220 nucleotide fragment. Primers F3 (5'-CAGGTAAG-GTCTAAAACGTGTGTTTGCTT) and R2 (5'-AATAAAGCTCAGGTGCCAGGCGAGGCGCTAT) covered the ND gene from +1720 to +2549 and generated an 830 nucleotide fragment.

Forward primers were prepared by mixing (1:4) IRDye™ 700-labeled primer:unlabeled primer with a concentration of 5 µM. Reverse primers were prepared by mixing (3:2) IRDye™ 800-labeled primer:unlabeled primer with a concentration of 5 µM. Stocked primers were prepared at 2:1 of Fwd:Rev ratio (5 µM total primer concentration). PCR amplification of the target region was done using 50-100 ng genomic DNA from pooled plant tissue DNA samples (in 10 µL reaction with 2 µL primer) and Platinum Taq DNA polymerase (Invitrogen, Catalogue no. 10966-034). PCR conditions were as follows: 1 cycle of 94° C. for two minutes, 40 cycles of 94° C. for one minute, 67° C. for one minute, 72° C. for 1.5 minutes, 1 cycle of 72° C. for ten minutes, and hold at 4° C. Following amplification, samples were heat denatured and reannealed (1 cycle of 95° C. for ten minutes, 95° C. to 85° C. at −2° C./second, and 85° C. to 25° C. at 0.1° C./second) to generate heteroduplexes between mutant amplicons and their wild-type counterparts.

Surveyor™ nuclease (Transgenomic®, Catalogue no. 706025) was used in accordance with kit recommendations to digest heteroduplexes. Nuclease incubation condition was 42° C. for twenty minutes and reactions were stopped by the addition of Stop Solution (Transgenomic® kit). Heteroduplexes were denatured with sequencing loading dye (98% deionized formamide, 10 mM EDTA (pH 8.0), 0.025% bromophenol blue) by heating 95° C. for two minutes. Denatured samples were chilled on ice and applied to denaturing polyacrylamide gel electrophoresis system. Electrophoresis was performed with a 6.5% KBPlus gel, run in a 18 cm plate assembly with 0.25 mm spacers on a LI-COR® DNA Analyzer (LI-COR® Biosciences) with running conditions of 1500-2000 V, 30 mA, 50 W and 45° C. for 3.5 hours.

In the polyacrylamide gel lanes that had a mutation in the pool, a band was visible below the wild type band on the IRDye™ 700 infrared dye image. A counterpart band was visible in the same lane on the IRDye™ 800 infrared dye image. This band was the cleavage product labeled with IRDye™ 800 infrared dye from the complementary DNA strand. The sum of the length of the two counterpart bands was equal to the size of the amplicon. After image analysis, the mutation pools (with deferred bands) were identified.

A second round of screening was performed on individual plants from pools in which a mutation was detected. Individual plant DNA from positive lines was extracted and combined with wild type DNA samples for the second round of screening. This helped to separate wild type and mutant plants (including homozygous and heterozygous mutants) within same $M_1$ pool. Samples with cleaved bands had a mutant ND gene sequence, while samples lacking a cleaved band had a wild type ND gene sequence.

A third round of screening was used to distinguish heterozygous from homozygous plants by using only mutant plant DNA as a template. The samples with no cleaved bands were homozygous. Sequence trace information was analyzed using the CEQ 8000 sequencer (Beckman, Fullerton, Calif.) to confirm the mutation. Using extracted DNA as the template, PCR amplification was performed to generate ND gene fragments for sequencing. PCR products were separated on a 1% agarose gel, purified, and sequenced.

The sequencing procedure was as follows: DNA was denatured by heating at 95° C. for 2 minutes, and subsequently placed on ice. The sequencing reaction was prepared on ice using 0.5 to 10 μL of denatured DNA template, 2 μL of 1.6 pmole of the forward primer, 8 μL of DTCS Quick Start Master Mix and the total volume brought to 20 μL with water. The thermocycling program consisted of 30 cycles of the follow cycle: 96° C. for 20 seconds, 50° C. for 20 seconds, and 60° C. for 4 minutes followed by holding at 4° C. The sequence was stopped by adding 5 μL of stop buffer (equal volume of 3M NaOAc and 100 mM EDTA and 1 μL of 20 mg/ml glycogen). The sample was precipitated with 60 μL of cold 95% ethanol and centrifuged at 6000 g for 6 minutes. Ethanol was discarded. The pellet was 2 washes with 200 μL of cold 70% ethanol. After the pellet was dry, 40 μL of SLS solution was added and the pellet was resuspended and overlaid with a layer of mineral oil. The sample was then placed sequenced (CEQ 8000 Automated Sequencer). The sequences were aligned with wild type sequence. In addition, the genomic nicotine demethylase DNA for several selected lines was sequenced to confirm that only single mutation for nicotine demethylase gene was present in each line.

After screening 700 independent $M_1$ pools, 19 mutated lines were identified. The mutation in each line is set forth in Table 1.

These mutated lines included one line with a truncated protein (TN90-4246), eleven lines with single amino acid changes (TN90-1849, TN90-1394, TN90-1761, TN90-4281, TN90-1516, TN90-1514, TN90-3320, TN90-3341, TN90-3387, TN90-1804, and TN90-1431) and seven lines with silent mutations (TN90-1777, TN90-1803, TN90-4264, TN90-1921, TN90-3147, TN90-4278, and TN90-4215). These lines were transplanted into a field for further characterization. Additional $M_1$ seeds from the same lines set forth in Table 1 were seeded and grown in the greenhouse to screen for more homozygous plants and for analysis of alkaloid content.

Example 3

Measurement of Nicotine Demethylation

Plant Materials and Induction Treatment

The selected $M_1$ mutant lines of Example 2 grown in the field were tested for their ability to convert nicotine to nornicotine. A middle position leaf from each $M_1$ plant at knee-high stage or later was sprayed with a 0.3% ethylene solution (Prep brand Ethephon (Rhone-Poulenc)) to induce nornicotine formation. Each sprayed leaf was hung in a plastic covered curing rack equipped with a humidifier. Sampled leaves were sprayed periodically with the ethylene solution throughout the treatment period. Approximately three days after the ethylene treatment, leaves were collected and dried in a oven at 50° C. for gas chromatographic (GC) analysis of alkaloids.

TABLE 1

Nicotine Demethylase Gene Mutations in EMS Mutated Tobacco (TN90)

| TOBACCO LINE | POSITION CHANGE[1] | CONTENT CHANGE | NOTE |
| --- | --- | --- | --- |
| TN90-4246 | +1985 nt from ATG +329 aa from M | G to A W329 Stop | Generated 329 aa nonsense mutation |
| TN90-1849 | +320 nt from ATG +107 aa from M | C to T P107L | Missense mutation in SRS-1 domain |
| TN90-1394 | +412 nt from ATG +138 aa from M | G to A V138I | Missense mutation |
| TN90-1761A | +934 nt from ATG +312 aa from ATG | G to A V312M | Missense mutation just before intron, in SRS-4 |
| TN90-4281 | +2191 nt from ATG +398 aa from M | G to A S 398 N | Missense mutation |
| TN90-1516 | +2307 nt from ATG +437 aa from M | G to A D437N | Missense mutation |
| TN90-1514 | +2307 nt from ATG +437 aa from M | G to A D437N | Missense mutation |
| TN90-3320 | +437 nt from ATG +146 aa from M | G to A S146N | Missense mutation |
| TN90-3341 | +704 nt from ATG +235 aa from M | C to T P235L | Missense mutation |
| TN90-3387 | +668 nt from ATG +230 aa from M | G to A D230N | Missense mutation |
| TN90-1804 | +244 nt from ATG +82 aa from M | C to T L82F | Missense mutation |
| TN90-1777 | +114 nt from ATG no aa change | C to T P38P | Silent mutation |
| TN90-1803 | +342 nt from ATG no aa change | C to T Y114Y | Silent mutation |
| TN90-4264 | +486 nt from ATG +163 aa from M | C to T S162S | Silent mutation |
| TN90-1921 | +2024 nt from ATG +343 aa from M | G to A K343K | Silent mutation |
| TN90-3147 | +429 nt from ATG no aa change | C to T L142L | Silent mutation |
| TN90-4278 | +2021 nt from ATG +342 aa no change | G to A T342T | Silent mutation |
| TN90-4215 | +2291 nt from ATG +431 aa no change | G to A E431E | Silent mutation |
| TN90-1431 | +2397 nt from ATG +467 aa from M | G to A E467K | Missense mutation |

[1]nt = nucleotide number and aa = amino acid residue number in SEQ ID NOS: 1 and 2.

Gas Chromatographic Alkaloid Analysis

GC alkaloid analysis was performed as follows: samples (0.1 g) were shaken at 150 rpm with 0.5 ml 2N NaOH, and a 5 ml extraction solution which contained quinoline as an internal standard and methyl t-butyl ether. Samples were analyzed on an HP 6890 GC (Hewlett Packard, Wilmington, Del., USA) equipped with a FID detector. A temperature of 250° C. was used for the detector and injector. An GC column (30m-0.32nm-1 m) consisting of fused silica cross-linked with 5% phenol and 95% methyl silicon was used at a temperature gradient of 110-185° C. at 10° C. per minute. The column was operated at a flow rate at 100° C. at 1.7 cm$^3$/min with a split ratio of 40:1 with a 2 µL injection volume using helium as the carrier gas. Percent nicotine demethylation was calculated as the amount of nicotine divided by the sum of the amounts of nicotine and nornicotine, multiplied by 100.

Table 2 shows the percent of plants having a non-converter phenotype and the mean percent nicotine demethylation for eight mutant lines, in relation to the genetic mutation status of individual plants of that line, including homozygous mutant, heterozygous mutant, and homozygous wild type. Four of the mutant lines had a percent nicotine demethylation of less than 5% in the $M_1$ generation and were classified as exhibiting a non-converter phenotype, mutant lines 4246, 1849, 4215 and 4278. The other four mutant lines had a percent nicotine demethylation of 5% or greater in the $M_1$ generation and were classified as having a converter phenotype, mutant lines 1394, 3320, 4264 and 1924.

TABLE 2

Nicotine Demethylation Levels in Nicotine Demethylase Mutant Lines

| EMS Line (TN90) | Status | Number of Plants | Mean % Nicotine Demethylation | % Converter Phenotype | % Non-converter Phenotype |
|---|---|---|---|---|---|
| 4246 | Homozygous | 11 | 0.85 | 0 | 100 |
| | Heterozygous | 36 | 51.47 | 94.45 | 5.6 |
| | Wild Type | 34 | 68.85 | 100 | 0 |
| | Total | 81 | | | |
| 1849 | Homozygous | 2 | 0.65 | 0 | 100 |
| | Heterozygous | 21 | 62.28 | 95.2 | 4.8 |
| | Wild Type | 2 | 71.2 | 100 | 0 |
| | Total | 25 | | | |
| 4215 | Homozygous | 4 | 0.025 | 0 | 100 |
| | Heterozygous | 12 | 43.32 | 100 | 0 |
| | Wild Type | 5 | 79.66 | 100 | 0 |
| | Total | 21 | | | |
| 4278 | Homozygous | 6 | 1.05 | 0 | 100 |
| | Heterozygous | 12 | 34.3 | 83.3 | 16.7 |
| | Wild Type | 2 | 82.1 | 100 | 0 |
| | Total | 20 | | | |
| 1394 | Homozygous | 1 | 96.8 | 100 | 0 |
| | Heterozygous | 2 | 88.6 | 100 | 0 |
| | Wild Type | 3 | 65.77 | 100 | 0 |
| | Unknown | 7 | 66.59 | 85.7 | 14.3 |
| | Total | 13 | | | |
| 3320 | Homozygous | 4 | 62.54 | 100 | 0 |
| | Heterozygous | 9 | 48.55 | 100 | 0 |
| | Wild Type | 6 | 62.03 | 100 | 0 |
| | Total | 19 | | | |
| 4264 | Homozygous | 2 | 83.6 | 100 | 0 |
| | Heterozygous | 3 | 59.27 | 100 | 0 |
| | Wild Type | 4 | 31.48 | 100 | 0 |
| | Total | 9 | | | |
| 1921 | Homozygous | 1 | 5.7 | 100 | 0 |
| | Heterozygous | 10 | 38.9 | 100 | 0 |
| | Wild Type | 0 | — | — | — |
| | Total | 11 | | | |

FIGS. 1A-1D show the frequency of converter and non-converter phenotypes among heterozygous mutant, homozygous mutant and homozygous wild-type $M_1$ plants for the mutant lines 4246, 1849, 4215, and 4278. FIGS. 1E and 1F show representative results for mutant lines in which there was no difference in nicotine demethylation among $M_1$ plants.

Example 4

RNA Expression Analysis in Nicotine Demethylase Mutant Lines

RNA from two lines was analyzed using semi-quantitative RT-PCR to measure their mRNA expression. About 20 individual $M_1$ plants from each line were ethylene treated as described in Example 3, and total RNA was extracted 3 days post-treatment. Total RNA was isolated using RNeasy Plant Mini Kit® (Qiagen, Inc., Valencia, Calif.) following the manufacturer's protocol. The tissue sample was ground under liquid nitrogen to a fine powder using a DEPC-treated mortar and pestle. Approximately 100 mg of ground tissue was transferred to a sterile 1.5 ml Eppendorf Tube® and the tube placed in liquid nitrogen until all samples were collected. Then, 450 µl of Buffer RLT as provided in the kit (with the addition of β-Mercaptoethanol) was added to each individual tube. The samples were vortexed vigorously and incubated at 56° C. for three minutes. The lysate was then applied to the QIAshredder™ spin column sitting in a 2-ml collection tube, and centrifuged for two minutes at maximum speed.

The flow through was collected and 0.5 volume of ethanol was added to the cleared lysate. The sample was mixed well and transferred to an Rneasy® mini spin column sitting in a 2 ml collection tube. The sample was centrifuged for one minute at 10,000 rpm. Next, 700 µl of buffer RW1 was pipetted onto the Rneasy® column and centrifuged for one minute at 10,000 rpm. Buffer RPE was pipetted onto the Rneasy® column in a new collection tube and centrifuged for one minute at 10,000 rpm. Buffer RPE was again added to the Rneasy® spin column and centrifuged for two minutes at maximum speed to dry the membrane.

To eliminate any ethanol carry over, the membrane was placed in a separate collection tube and centrifuged for an additional one minute at maximum speed. The Rneasy® column was transferred into a new 1.5 ml collection tube, and 40 µl of Rnase-free water was pipetted directly onto the Rneasy® membrane. This final elute tube was centrifuged for one minute at 10,000 rpm. Quality and quantity of total RNA was analyzed by denatured formaldehyde gel and spectrophotometer.

First strand cDNA was produced using SuperScript™ reverse transcriptase following manufacturer's protocol (Invitrogen, Carlsbad, Calif.). About 100 ng of total RNA was used for first strand cDNA generation.

RT-PCR was carried out with 100 pmoles each of forward and reverse primers. Reaction conditions were 94° C. for two minutes and then 40 cycles of PCR at 94° C. for one minute, 67° C. for one minute, 72° C. for three minutes, followed by a single extension at 72° C. for ten minutes. Fifty microliters of the amplified sample were analyzed by electrophoresis using a 1% agarose gel.

The agarose gels were stained using ethidium bromide and the amount of ND RNA present was classified as low or high based on band intensity. Selected samples were sliced and purified from the agarose gel. The purified DNA was sequenced by CEQ 8000 as described above.

Example 5

Nicotine Demethylase Sequence Analysis

The amino acid sequence set forth in SEQ ID NO:2 was subjected to analysis using the TFSEARCH program (cbrc.jp/htbin/nph-tfsearch) and the Web Signal Scan Program (dna.affrc.gojp/sigscan) to identify regulatory region elements (e.g., TATA and CAAT boxes), organ-specific elements, and WRKY elements. As shown in FIG. 2, the analysis indicated that SEQ ID NO:2 contains six substrate recognition sites (SRS) at amino acids 108-129, 212-220, 249-256, 312-326, 380-390, and 491-497, an N-terminal hydrophobic transmembrane domain at amino acids 9-20, a proline-rich region at amino acids 34-38, a threonine-containing oxygen-binding pocket at amino acids 346-351, a K-helix consensus at amino acids 353-356, a PERF consensus at amino acids 430-433, and a cysteine-containing heme-binding region at amino acids 450-459.

Example 6

Nicotine Conversion Stability in Nicotine Demethylase Mutant Lines

Large scale field trials were conducted with selected $M_2$ mutant lines, 4246-8 and 1859-8B, using a screened low converter (LC) Certified commercial variety (TN90-LC) and its high converter counterpart (TN90-C) as controls. The screened LC Certified variety is commercially available from F.W. Rickard Seeds (Winchester, Ky.). Screened LC Certified seed is collected from plants grown from screened LC Foundation seed. Screened LC Foundation seed is collected from a population of tobacco plants from which plants with a nicotine conversion level higher than 3% were removed, and from which any flowers or capsules that were produced prior to removing the plants having a nicotine conversion level higher than 3% were removed.

Two $M_2$ mutant lines, 4246-8 and 1859-8B, were produced through self pollination of $M_1$ homozygous mutant plants. These lines were grown in 3 field trials with total population of about 200 plants per line. The plants grown in the field were tested for their ability to convert nicotine to nornicotine. A middle position leaf from each $M_2$ plant was ethylene treated as described in Example 3. Approximately three days after the ethylene treatment, leaves were collected and dried in an oven at 50° C. for gas chromatographic (GC) analysis of alkaloids as described in Example 3.

Table 3 shows the nicotine conversion stability in $M_2$ mutant lines in comparison of commercial LC line and converter control. Mutant line 4246-8 had mean percentage nicotine conversion of 1.9% and had no plants that were classified as high converter. Mutant line 1849-8B had mean percentage conversion of 2.1% and had 3 plants from total of 214 that were classified as high converters. The LC and converter lines had mean conversion of 6.6% and 80.6%, respectively, and had 24% and 100% of the plants, respectively, classified as high converters.

The $M_3$ generation had a similar low frequency of conversion, demonstrating the stability of the low-converter phenotype in the mutant lines.

TABLE 3

Nicotine Demethylation Levels in Nicotine Demethylase Mutant $M_2$ Lines, Screened Low Converter and Converter Controls

| Line | Number of Plants | Number of Converters | Converters (% of Population) | Average Conversion Rate (%) |
|---|---|---|---|---|
| 4246-8 | 184 | 0 | 0 | 1.9 |
| 1849-8B | 212 | 3 | 1.4 | 2.1 |
| TN90-LC | 218 | 53 | 24.3 | 6.6 |
| TN90-C | 95 | 95 | 100 | 80.6 |

Example 7

Detection of Tobacco Specific Nitrosamine Formation in Nicotine Demethylase Mutant Lines Large scale field trials were conducted with selected $M_2$ mutant lines, 4246-8 and 1859-8B, using screened low converter (LC) Certified commercial variety (TN90-LC) and its high converter counterpart (TN90-C) as controls as described in Example 6.

The field grown plants from Example 6 were grown to maturity, and were harvested and air-cured using standard tobacco production practices. The tobacco chemistry was analyzed by gas-chromatographic-TAE analysis. Table 4 depicts the tobacco specific nitrosamine (TSNA) content of mutant lines in comparison to LC and converter controls. The N-nitrosonornicotine (NNN) content, which is directly derived from nornicotine, and total TSNA content in mutant lines were lower than those in TN90-LC and TN90-converter lines.

TABLE 4

N-nitrosonornicotine (NNN) and Total Tobacco Specific Nitrosamine (TSNA) Levels in Air-cured Burley Tobacco Mutant Lines

| Line | NNN (ppm) | Total TSNA (ppm) |
|---|---|---|
| 4246-8 | 0.7 | 0.9 |
| 1849-8B | 0.8 | 0.9 |
| TN 90 Empty Vector | 1.6 | 1.9 |
| TN 90-LC | 1.6 | 1.6 |
| TN 90-C (high converter) | 5.5 | 5.6 |

Example 8

Nicotine Demethylase RNA Interference

Ti nicotine demethylase RNA interference (RNAi) constructs were constructed using fragments of a nicotine demethylase nucleic acid sequence (SEQ ID NO:1) such that each Nicotine demethylase RNAi construct contained a cassava vein mosaic virus promoter (CsVMV) operably linked to a nicotine demethylase nucleic acid fragment (SEQ ID NO:5, SEQ ID NO:6, SEQ ID NO:7, or SEQ ID NO:8) in antisense orientation relative to the promoter, followed by a loop sequence, the complement of the respective fragment, and a Nos terminator as indicated in FIG. 3. Each nicotine demethylase RNAi construct contained a neomycin phosphotransferase II gene operably linked to an *Arabidopsis thaliana* Actin 2 promoter and a Nos terminator. See, FIG. 3. Sequences present in nicotine demethylase RNAi constructs are shown in Table 5.

TABLE 5

Nucleic acid sequences used to construct nicotine demethylase RNAi constructs

| Nicotine demethylase RNAi construct | Stem sequence | Loop sequence |
|---|---|---|
| pGen-RNAi1-IN | SEQ ID NO: 5 | NDM Intron (SEQ ID NO: 9) |
| pGen-RNAi1-gus | SEQ ID NO: 5 | gus fragment in antisense orientation (SEQ ID NO: 10) |
| pGEN-RNAi2-AT | SEQ ID NO: 6 | *Arabidopsis thaliana* Actin II intron 2 (SEQ ID NO: 11) |
| pGEN-RNAi3-IN | SEQ ID NO: 7 | NDM Intron (SEQ ID NO: 9) |
| pGEN-RNAi4-AT | SEQ ID NO: 8 | *Arabidopsis thaliana* Actin II intron 2 (SEQ ID NO: 11) |

Each Nicotine demethylase RNAi construct was introduced into Narrow Leaf Madole dark tobacco and TN 90 burley tobacco using standard *Agrobacterium* transformation. Briefly, leaf tissue from 4-week-old aseptically-grown plants was cut into pieces and incubated in liquid medium containing *A. tumefaciens* (strain LB4404) with the desired constructs. The tissue was allowed to grow on basal medium without antibiotics for two days to enhance tissue infection. On the third day, the tissue was plated on media containing kanamycin (300 mg/L), for transformant selection, and Cetofexin (500 mg/L) to kill the remaining *A. tumefaciens*. The culture media was replaced each week until callus tissue developed. Shoots derived from the callus tissue were transferred to rooting media for rooting, and subsequently, rooted plantlets were transplanted into 4 inch pots containing commercial soil mix. Plants were grown to maturity in a greenhouse and self-pollinated.

As used herein, "$R_0$" refers to plant cells (and plants grown therefrom) transformed with an exogenous nucleic acid, while "$R_1$" refers to seeds produced by self-pollinated $R_0$ plants, and plants grown from such seeds. "$R_2$" is the progeny (seeds and plants) of self-pollinated $R_1$ plants, "$R_3$" is the progeny of self-pollinated $R_2$ plants, and "$R_4$" is the progeny of self-pollinated $R_3$ plants. "$R_5$" is the progeny of self-pollinated $R_4$ plants. "$R_6$", "$R_7$", etc. are each the progeny of self-pollinated plants of the previous generation.

Screening and Regeneration of Transgenic Lines $R_1$ seeds derived from selfing the primary transformants were germinated and grown on media containing 300 mg/L kanamycin. The number of kanamycin resistant and sensitive seedlings was determined 2-3 weeks after germination when the sensitive seedlings were chlorotic and unable to produce true leaves. These data were used to identify segregation pattern. Plants resistant to kanamycin were grown to maturity in a greenhouse and self-pollinated. Seed was collected from each plant and sown on media containing kanamycin to determine which $R_1$ plants were homozygous for the transgene.

Seeds from each transgenic RNAi line were planted in the field, and conversion of nicotine to nornicotine was measured and compared to three controls for each tobacco variety: 1. tobacco plants containing an empty vector (i.e., a vector lacking a nicotine demethylase nucleic acid fragment, a loop sequence, and a nicotine demethylase fragment complementary sequence); 2. plants from a commercially available LC line (i.e., Narrow Leaf Madole LC Certified seed (F.W. Rickard Seeds, Winchester, Ky.) for the Narrow Leaf Madole transgenic plants and TN 90-LC Certified seed for the TN 90 transgenic plants); and 3. plants from a high converter line (i.e., 181 CK for the Narrow Leaf Madole transgenic plants and TN 90-C for the TN 90 transgenic plants). A dark tobacco plant was identified as a converter if its conversion rate was 3% or greater. A burley tobacco plant was identified as a converter if its conversion rate was 5% or greater. The results are shown in Tables 6 and 7.

TABLE 6

Conversion of nicotine to nornicotine in transgenic Narrow Leaf Madole dark tobacco

| Tobacco line | Vector | Average percent conversion | Percent converters in population |
|---|---|---|---|
| NLM-IN5-44 | pGen-RNAi1-IN | 0.1 | 0 |
| NLM-IN5-52 | pGEN-RNAi1-IN | 0.2 | — |
| NLM-2IN-22 | pGen-RNAi3-IN | 0.2 | — |
| NLM-2IN-38 | pGEN-RNAi3-IN | 0.3 | 0 |
| NLM-2AT-33 | pGen-RNAi2-AT | 0.4 | 0 |
| NLM-2AT-32 | pGEN-RNAi2-AT | 0.4 | 0 |
| NLM-3AT-11 | pGEN-RNAi4-AT | 0.5 | — |
| NLM-G2-2 | pGEN-RNAi1-gus | 0.5 | — |
| NLM-vector | Empty Vector | 1.7 | — |
| NL Madole LC | — | 1.5 | 5 |
| 181 CK | — | 95.1 | 100 |

TABLE 7

Conversion of nicotine to nornicotine in transgenic TN 90 burley

| Tobacco line | Vector | Average percent conversion | Percent converters in population |
|---|---|---|---|
| TN90-IN5-14 | pGen-RNAi1-IN | 0.6 | 0 |
| TN90-IN5-22 | pGEN-RNAi1-IN | 1.1 | — |
| TN90-2IN-12 | pGen-RNAi3-IN | 1.2 | — |
| TN90-2AT-4 | pGEN-RNAi2-AT | 2.7 | — |
| TN90-2AT-5 | pGen-RNAi2-AT | 2.8 | — |
| TN90-G2-7 | pGEN-RNAi1-gus | 4.6 | — |
| TN90-vector | Empty Vector | 4.2 | — |
| TN90 LC | — | 6.5 | 24 |
| TN90 C | — | 63.7 | 100 |

Nicotine demethylase RNA expression was measured relative to nicotine demethylase RNA expression in TN 90-LC using quantitative RT-PCR. The results are shown in Table 8.

TABLE 8

Relative NDM mRNA expression

| Tobacco line | NDM mRNA expression relative to TN 90-LC |
|---|---|
| Narrow Leaf Madole IN5 | 0.1 |
| Narrow Leaf Madole 2IN | 0.1 |
| Narrow Leaf Madole 2IN-1 | not detectable |
| TN 90 2AT | 0.1 |
| TN 90 G2 | not detectable |
| TN 90-LC | 1.0 |

TABLE 8-continued

Relative NDM mRNA expression

| Tobacco line | NDM mRNA expression relative to TN 90-LC |
|---|---|
| TN 90-C (high converter) | 3.1 |
| 181 CK (high converter) | 6.6 |

Example 9

Detection of Tobacco Specific Nitrosamine Formation in Nicotine Demethylase RNAi Lines Large scale field trials were conducted with selected NDM RNAi lines NLM-IN5-44, NLM-IN5-52, NLM-2IN-22, NLM-2IN-38, NLM-2AT-33, NLM-2AT-32, NLM-3AT-11, TN90-IN5-14, TN90-IN5-22, TN90-2IN-12, TN90-2AT-4, TN90-2AT-5, and TN90-G2-7 using the respective empty vector transformed varieties, the respective screened low converter (LC) Certified commercial varieties (i.e., Narrow Leaf Madole LC and TN 90-LC), and the respective high converter counterpart (i.e., 181 and TN90-C) as controls. LC seeds were produced as described in Example 7. Six RNAi TN 90 lines and eight RNAi Narrow Leaf Madole lines that were produced through self pollination of $R_1$ homozygous transgenic plants were used to measure tobacco specific nitrosamine (TSNA) levels.

About 200 plants per line were grown to maturity in 3 field trials. The plants were harvested and cured as indicated in Tables 9-11 using standard techniques. The tobacco chemistry was analyzed by gas-chromatographic-TAE analysis. Tables 9-11 show the N-nitrosonornicotine levels and total tobacco specific nitrosamines (TSNAs) of RNAi lines in comparison to empty vector, LC, and converter controls. The data indicates that N-nitrosonornicotine (NNN) levels and total TSNA levels in NDM RNAi lines were lower than in the control lines.

TABLE 9

NNN and Total TSNA Levels in Fire-cured Dark Tobacco RNAi Lines

| Line | Vector | NNN (ppm) | Total TSNA (ppm) |
|---|---|---|---|
| NLM-IN5-44 | pGen-RNAi1-IN | 0.196 | 1.003 |
| NLM-IN5-52 | pGEN-RNAi1-IN | 0.19 | 1.069 |
| NLM-2IN-22 | pGen-RNAi3-IN | 0.337 | 1.22 |
| NLM-2IN-38 | pGEN-RNAi3-IN | 0.338 | 1.414 |
| NLM-2AT-33 | pGen-RNAi2-AT | 0.288 | 1.113 |
| NLM-2AT-32 | pGEN-RNAi2-AT | 0.254 | 1.321 |
| NLM-3AT-11 | pGEN-RNAi4-AT | 0.323 | 1.428 |
| NLM-G2-2 | pGEN-RNAi1-gus | 0.318 | 1.456 |
| NLM-vector | Empty Vector | 0.791 | 1.606 |
| NL Madole LC | — | 0.952 | 2.041 |
| 181 CK | — | 18.696 | 20.488 |

TABLE 10

NNN and Total TSNA Levels in Air-cured Dark Tobacco RNAi Lines

| Line | Vector | NNN (ppm) | Total TSNA (ppm) |
|---|---|---|---|
| NLM-IN5-44 | pGen-RNAi1-IN | 0.093 | 0.254 |
| NLM-IN5-52 | pGEN-RNAi1-IN | 0.186 | 0.567 |
| NLM-2IN-22 | pGen-RNAi3-IN | 0.195 | 0.595 |
| NLM-2IN-38 | pGEN-RNAi3-IN | 0.166 | 0.394 |
| NLM-2AT-33 | pGen-RNAi2-AT | 0.205 | 0.762 |
| NLM-2AT-32 | pGEN-RNAi2-AT | 0.112 | 0.439 |
| NLM-3AT-11 | pGEN-RNAi4-AT | 0.142 | 0.373 |
| NLM-G2-2 | pGEN-RNAi1-gus | 0.165 | 0.681 |
| NLM-vector | Empty Vector | 3.673 | 5.597 |
| NL Madole LC | — | 0.617 | 1.167 |
| 181 CK | — | 8.756 | 10.909 |

TABLE 11

NNN and Total TSNA Levels in Air-cured Burley Tobacco RNAi Lines

| Line | Vector | NNN (ppm) | Total TSNA (ppm) |
|---|---|---|---|
| TN90-IN5-14 | pGen-RNAi1-IN | 0.239 | 0.365 |
| TN90-IN5-22 | pGEN-RNAi1-IN | 0.573 | 1.689 |
| TN90-2IN-12 | pGen-RNAi3-IN | 0.708 | 0.785 |
| TN90-2AT-4 | pGEN-RNAi2-AT | 0.335 | 0.472 |
| TN90-2AT-5 | pGen-RNAi2-AT | 0.435 | 0.763 |
| TN90-G2-7 | pGEN-RNAi1-gus | 0.892 | 1.091 |
| TN90-vector | Empty Vector | 1.635 | 1.869 |
| TN90 LC | — | 1.552 | 1.606 |
| TN90 C | — | 5.523 | 5.572 |

Example 10

Phenotypic Characteristics in Nicotine Demethylase Mutant and RNAi Lines

Large scale field trials of nicotine demethylase mutant and RNAi lines were grown to maturity as described in Examples 7 and 9. Plant height, leaf length, leaf width, and yield were measured. The results are shown in Tables 12-14.

TABLE 12

Phenotypic Characteristics of Dark Tobacco RNAi Lines

| Line | Vector | Plant height-topped (cm) | Plant height-not topped (cm) | $10^{th}$ leaf length (cm) | $10^{th}$ leaf width (cm) | Yield (lbs/acre) Fire cured | Yield (lbs/acre) Air cured |
|---|---|---|---|---|---|---|---|
| NLM-IN5-44 | pGen-RNAi1-IN | 108 | 130 | 79 | 40 | 3583 | 3508 |
| NLM-IN5-52 | pGEN-RNAi1-IN | 110 | 129 | 80 | 39 | 3436 | 3340 |
| NLM-2IN-22 | pGen-RNAi3-IN | 106 | 115 | 77 | 37 | 3476 | 3495 |
| NLM-2IN-38 | pGEN-RNAi3-IN | 109 | 128 | 79 | 38 | 3330 | 3301 |
| NLM-2AT-33 | pGen-RNAi2-AT | 112 | 130 | 78 | 39 | 3634 | 3480 |
| NLM-2AT-32 | pGEN-RNAi2-AT | 110 | 130 | 79 | 39 | 3089 | 3416 |
| NLM-3AT-11 | pGEN-RNAi4-AT | 106 | 128 | 77 | 33 | 3426 | 3381 |
| NLM-G2-2 | pGEN-RNAi1-gus | 109 | 130 | 80 | 39 | 3450 | 3256 |
| NLM-vector | Empty Vector | 108 | 129 | 76 | 35 | 3445 | 3587 |
| NL Madole LC | — | 111 | 132 | 80 | 39 | 3567 | 3474 |
| 181 CK | — | 114 | 132 | 77 | 44 | 3616 | 3233 |

TABLE 13

Phenotypic Characteristics of Burley Tobacco RNAi Lines

| Line | Vector | Plant height-topped (cm) | Plant height-not topped (cm) | 10$^{th}$ leaf length (cm) | 10$^{th}$ leaf width (cm) | Yield (lbs/acre) |
|---|---|---|---|---|---|---|
| TN90-IN5-14 | pGen-RNAi1-IN | 139 | 179 | 68 | 36 | 3316 |
| TN90-IN5-22 | pGEN-RNAi1-IN | 138 | 178 | 68 | 40 | 3200 |
| TN90-2IN-12 | pGen-RNAi3-IN | 139 | 177 | 69 | 39 | 3125 |
| TN90-2AT-4 | pGEN-RNAi2-AT | 140 | 179 | 70 | 40 | 3207 |
| TN90-2AT-5 | pGen-RNAi2-AT | 141 | 180 | 70 | 42 | 3237 |
| TN90-G2-7 | pGEN-RNAi1-gus | 132 | 174 | 70 | 40 | 3088 |
| TN90-vector | Empty Vector | 139 | 179 | 70 | 39 | 3269 |
| TN90 LC | — | 138 | 179 | 70 | 39 | 3361 |
| TN90 C | — | 141 | 182 | 69 | 40 | 3175 |

TABLE 14

Phenotypic Characteristics of Burley Tobacco Mutant Lines

| Line | Plant height-topped (cm) | Plant height-not topped (cm) | 10$^{th}$ leaf length (cm) | 10$^{th}$ leaf width (cm) | Yield (lbs/acre) |
|---|---|---|---|---|---|
| 4246-8 | 118 | 146 | 62 | 32 | 2904 |
| 1849-8B | 112 | 138 | 60 | 34 | 2944 |
| TN90 LC | 138 | 179 | 70 | 39 | 3361 |
| TN90 C | 141 | 182 | 69 | 40 | 3175 |

Example 11 Production of Mutant NLM *Nicotiana* Plants

Narrow Leaf Madole (NLM) dark tobacco low-converter lines were used for mutagenesis. Seeds of each line were screened using standard techniques to remove converter seeds. Screened seeds of the lines had an average percent conversion of nicotine to nornicotine of about 1.5 to 1.9%.

A first population of mutant NLM plants was made as follows. NLM low-converter seeds were mutagenized with ethylmethane sulfonate (EMS, Sigma Catalogue No. M-0880) essentially as described in Example 1 above. The resulting plants were transplanted into a field and self-pollinated, seeds were harvested from each of about 5,000 plants, and individual "D" designations were given to the set of seeds from each plant. M$_1$ plants were selfed in the field and M$_2$ seeds harvested. Plants from the M$_2$ seeds formed the first population.

About 0.7 gram of seeds (approximately 7,000 seeds) of a second population of NLM low-converter seeds of a line containing a ph gene conferring resistance to Blackshank Race 0 were mutagenized in the same manner, except that the seeds were incubated with 0.6% EMS for about 15 hours. About 100 of the resulting M$_1$ plants were grown in a greenhouse and given individual "N" designations. These plants formed the second population.

Example 12

Identification of Mutations in CYPE82E4 and CYPE82E5

DNA was extracted from leaves from each M$_1$ or M$_2$ individual and analyzed for the presence of mutations in CYP82E4 and E5 essentially as described in Example 2 above. The primer pairs used for CYP82E4 were the same as those used in Example 2 above. The primer pairs used for CYP82E5 are shown as SEQ ID NOs:14-17.

Twenty-two lines were identified with mutations in the CYP82E4 gene and 15 lines were identified with mutations in the CYP82E5 gene from plants from the first population and plants from the second population. The position of the mutation, nucleotide change, and amino acid change, if any, in the CYP82E4 mutant lines and for the CYP82E5 mutant lines is set forth in Tables 15 and 16, respectively.

TABLE 15

Mutations in the CYP82E4 Gene in Mutant NLM Tobacco Lines

| Tobacco Line | Position of Mutation[1] | Nucleotide change | Amino Acid Change | Amino Acid Residue |
|---|---|---|---|---|
| D-6 | 840 | G to A | No change | 280 |
| D-26 | 2102 | C to T | Nochange | 368 |
| D-84 | 336 | C to T | No change | 112 |
| D-623 | 216 | C to T | Nochange | 73 |
| D-641 | 2289 and 763 | G to A and G to A | E to K and D to N | 431 and 255 |
| D-656 | 290 | C to T | S to F | 96 |
| D-699 | 2454 | G to A | E to K | 486 |
| D-709 | 2124 | G to A | V to M | 376 |
| D-1738 | 823 | G to A | E to K | 275 |
| D-1745 | 934 | G to A | V to M | 312 |
| D-1791 | 204 | C to T | No change | 68 |
| D-1793 | 2307 | G to A | D to N | 437 |
| D-1809 | 697 | C to T | P to S | 233 |
| D-1863 | 579 | G to A | No change | 193 |
| D-1915 | 244 | C to T | L to F | 82 |
| D-1945 | 687 | G to A | W to Stop | 229 |
| D-1946 | 2205 | C to T | P to S | 403 |
| D-2462 | 2440 | G to A | R to K | 481 |
| D-3096 | 170 | G to A | R to H | 57 |
| D-3368 | 717 | G to A | W to Stop | 239 |
| N-5 | 747 | G to A | M to I | 249 |
| N-21 | 268 | G to A | E to K | 90 |

[1]Nucleotides from ATG start codon in SEQ ID NO: 1.

TABLE 16

Mutations in the CYP82E5 Gene in Mutant NLM Tobacco Lines

| Tobacco Line | Position Of Mutation[1] | Nucleotide Change | Amino Acid Change | Amino Acid Residue |
|---|---|---|---|---|
| D-25 | — | G to A | G to R | 453 |
| D-102 | — | G to A | No change | 443 |
| D-108 | 386 | C to T | P to L | 129 |
| D-3077 | 807 | G to A | No change | 269 |
| D-3085 | 204 | C to T | No change | 68 |
| D-3087 | 747 | O to T | M to I | 249 |
| N-2 | — | C to T | No change | 439 |
| N-6 | — | C to T | R to C | 499 |
| N-45 | — | G to A | I to V | 373 |
| N-51 | 550 | G to A | E to K | 184 |
| N-79 | — | G to A | W to Stop | 329 |
| D-339 | 688 | G to A | D to N | 230 |
| D-948 | 686 | G to A | W to Stop | 229 |
| D-1821 | 521 | C to T | S to L | 174 |
| D-2126 | 61 | C to T | No change | 21 |

[1]Nucleotides from ATG start codon in SEQ ID NO: 12.

Example 13

Measurement of Nicotine Demethylation

Plant Materials and Induction Treatment

Two of the CYP82E4 mutant lines (D-1945, and D-3368) of Example 12 were chosen for analysis of alkaloid content. The lines were grown in the field and green leaf tissue was analyzed for nornicotine formation (with and without ethylene induction) by collecting a middle position leaf from each $M_1$ plant at knee-high stage and measuring nicotine and nornicotine content by gas chromatographic (GC) analysis essentially as described in Example 3 above.

Figure 4:
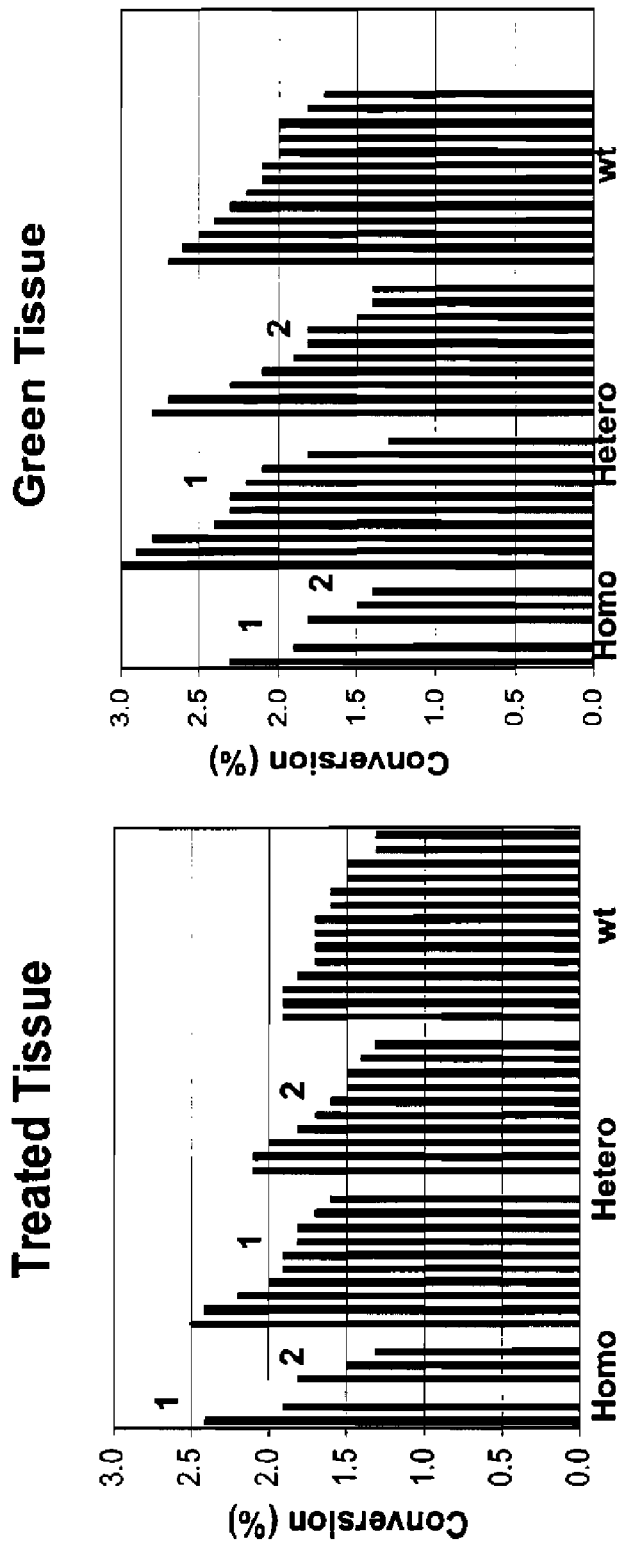
FIG. 4 is a bar graph showing the percent conversion of nicotine to nornicotine as measured by gas chromatography of leaves from mutant NLM tobacco lines versus genotype at the CYP82E4 locus. 1: Mutant Line NLM D-1945, 2: Mutant Line NLM D-3368. "Homo" indicates plants homozygous and "Hetero" indicates plants heterozygous for the mutant allele at the CYP82E4 nicotine demethylase locus. "Wild" indicates NLM plants homozygous for wild-type nicotine demethylase CYP82E4. "Treated Tissue" indicates leaves that have been treated with ethylene prior to analysis. "Green Tissue" indicates leaves that have not been treated with ethylene.
Figure 5:
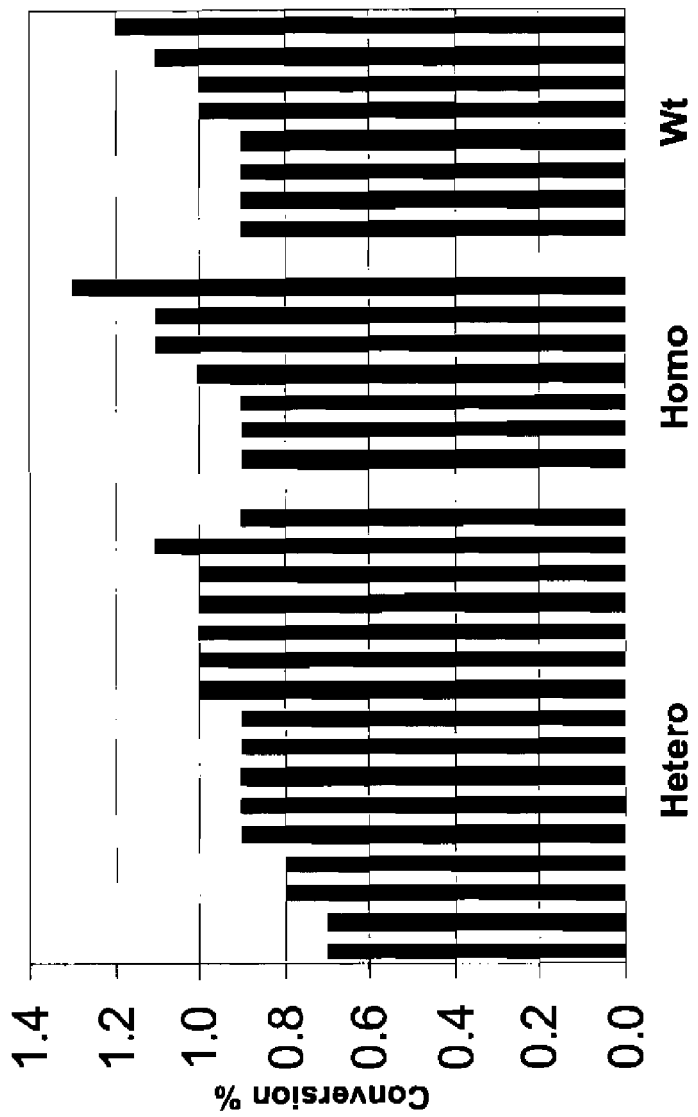
FIG. 5 is a bar graph showing the percent conversion of nicotine to nornicotine as measured by gas chromatography in green leaves of mutant NLM tobacco line NLM-N79 relative to genotype at the CYP82E5 locus. "Hetero" indicates plants heterozygous and "Homo" indicates plants homozygous for the mutant allele at the CYP82E5 nicotine demethylase locus. "Wild" indicates NLM plants homozygous for wild-type nicotine demethylase CYP82E5.
Figure 6:
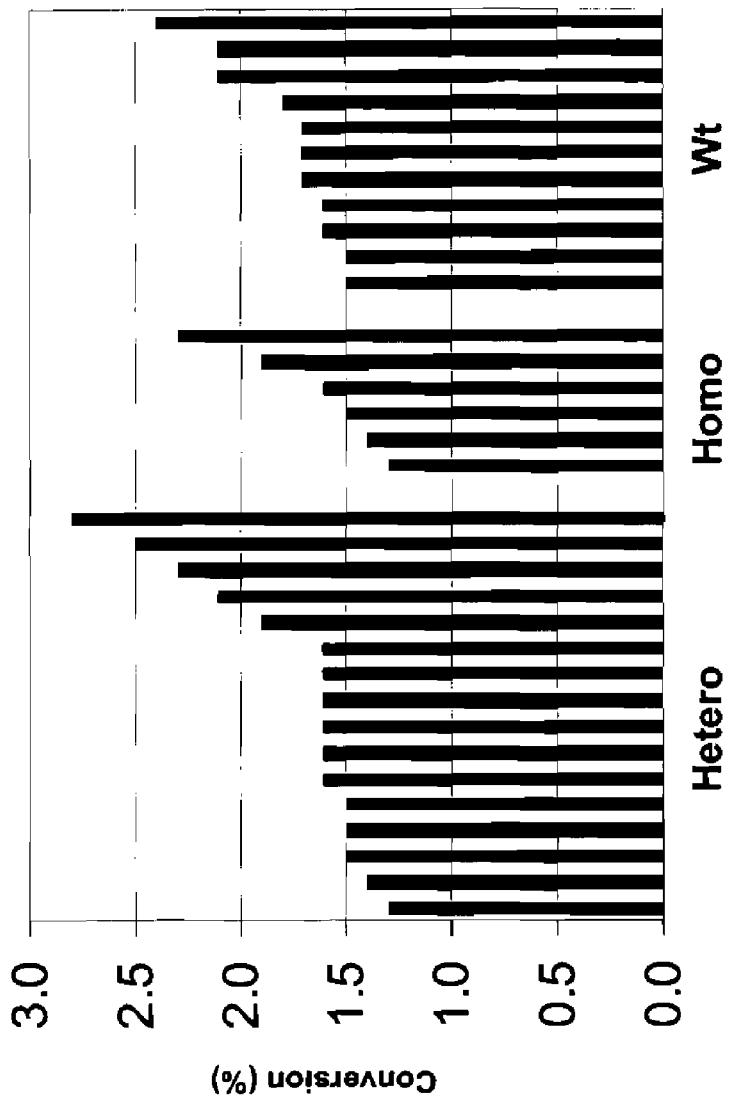
FIG. 6 is a bar graph showing the percent conversion of nicotine to nornicotine as measured by gas chromatography in green leaves of mutant NLM tobacco line NLM-948 relative to genotype at the CYP82E5 locus. "Hetero" indicates plants heterozygous and "Homo" indicates plants homozygous for the mutant allele at the CYP82E5 nicotine demethylase locus. "Wild" indicates NLM plants homozygous for wild-type nicotine demethylase CYP82E5.

Two of the CYP82E5 mutant lines (D-948 and N-79) were also analyzed for nornicotine formation in green leaf tissues. Percent conversion of nicotine to nornicotine was calculated as the amount of nicotine divided by the sum of the amounts of nicotine and nornicotine, multiplied by 100, and the results plotted as bar graphs as shown in FIGS. 4-6.

The results indicated that the percent conversion in heterozygous and homozygous E4 mutant plants of D-1945 and D-3368 was about 1.2% to 2.4%, and was not significantly different from the percent conversion observed for homozygous wild-type NLM low-converter plants. See FIG. 4. The results indicated that the percent conversion for heterozygous and homozygous E5 mutant plants of D-948 and N-79 was about 0.7% to 2.7%, and was not significantly different from the percent conversion observed for homozygous wild-type NLM low-converter plants. See FIGS. 5 and 6.

Example 14

Analysis of the CYP82E4 Promoter

The pattern of the CYP82E4 gene expression was analyzed in the E5 mutant line D-948 by quantitative RT-PCR of endogenous expression. The results indicated that the E4 gene is expressed at a low level in green tissue. E4 promoter expression was analysed by transformation of tobacco with a chimeric E4 promoter::β-glucuronidase (GUS) reporter gene. The chimeric gene was introduced via *Agrobacterium*-mediated transformation into a Burley low converter line, a Burley converter line and an Oriental tobacco low converter line. The results indicated that the E4 promoter drives expression of the GUS gene at a low level in green tissue in the absence of ethylene induction. GUS gene expression increased after the ethylene treatment.

What is claimed is:

1. A tobacco hybrid comprising plants having a mutant allele at a nicotine demethylase locus, said mutant allele encoding the amino acid sequence shown in SEQ ID NO:2, wherein the tryptophan at amino acid 329 is replaced with a stop codon.

2. The hybrid of claim 1, wherein said tobacco hybrid is a *Nicotiana tabacum* hybrid.

3. A method of making a tobacco plant, comprising the steps of:
   a) inducing mutagenesis in cells of a *Nicotiana* species;
   b) obtaining one or more plants from said cells;
   c) identifying at least one of said plants that contains a nicotine demethylase gene
      encoding the amino acid sequence set forth in SEQ ID NO:2, wherein the tryptophan at amino acid 329 is replaced with a stop codon.

4. The method of claim 3, further comprising the steps of:
   crossing said plant containing said at least one mutation in said nicotine demethylase gene with a second *Nicotiana* plant; and
   selecting progeny of said cross that have said at least one mutation in said nicotine demethylase gene.

5. The method of claim 3, wherein said cells are in a seed.

6. A method for producing a tobacco plant comprising the steps of:
   a) providing a first tobacco plant having a mutation in an endogenous nicotine demethylase gene having the sequence shown in SEQ ID NO:2 and a second tobacco plant that contains a desired phenotypic trait, wherein the mutation is a stop codon at residue 329;
   b) crossing said first tobacco plant with said second tobacco plant to produce one or more $F_1$ progeny plants;
   c) collecting seed produced by said $F_1$ progeny plants; and
   d) germinating said seed to produce tobacco plants having decreased expression of a nicotine demethylase gene.

7. The method of claim 6, wherein said first tobacco plant is *Nicotiana tabacum*.

8. The method of claim 6, wherein said first tobacco plant is an Oriental tobacco plant, a dark tobacco plant, a flue-cured tobacco plant, an air-cured tobacco, a Virginia tobacco plant or a Burley tobacco plant.

9. The method of claim 6, wherein said second tobacco plant is *Nicotiana tabacum*.

10. The method of claim 6, wherein said second tobacco plant is an Oriental tobacco plant, a dark tobacco plant, a flue-cured tobacco plant, an air-cured tobacco plant, a Virginia tobacco plant or a Burley tobacco plant.

11. The method of claim 6, wherein said desired phenotypic trait is selected from the group consisting of disease resistance; high yield; high grade index; curability; curing quality; mechanical harvestability; holding ability; leaf quality; height; maturation; stalk size; and leaf number per plant.

12. The method of claim 6, wherein said second tobacco plant is a male sterile variety or a male sterile hybrid.

13. The method of claim 12, further comprising the step of backcrossing said tobacco plants produced from germinated seed of step (d) to plants of said male sterile variety or male sterile hybrid.

14. Cured tobacco made from the hybrid of claim 1.

15. The cured tobacco of claim 14, wherein said tobacco is made by a curing process selected from the group consisting of flue curing, air curing, fire curing and sun curing.

16. A tobacco product comprising the cured tobacco of claim 14.

17. The tobacco product of claim 16, wherein said tobacco product is selected from the group consisting of a cigarette product, a cigar product, a pipe tobacco product, a smokeless tobacco product, a film, a tab, a gel, a shaped part, a rod and a foam.

18. A tobacco variety comprising plants having a mutant allele at a nicotine demethylase locus, said mutant allele encoding the amino acid sequence shown in SEQ ID NO:2, wherein the tryptophan at amino acid 329 is replaced with a stop codon.

* * * * *

UNITED STATES PATENT AND TRADEMARK OFFICE
CERTIFICATE OF CORRECTION

| | |
|---|---|
| PATENT NO. | : 8,319,011 B2 |
| APPLICATION NO. | : 12/484975 |
| DATED | : November 27, 2012 |
| INVENTOR(S) | : Dongmei Xu et al. |

It is certified that error appears in the above-identified patent and that said Letters Patent is hereby corrected as shown below:

On the Title Page, Item [63], Related U.S. Application Data, line 2, please replace "2007" with --2007, which is a Continuation-in-Part of U.S. Application No. 11/611,782, filed on Dec. 15, 2006.--.

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,319,011 B2
APPLICATION NO. : 12/484975
DATED : November 27, 2012
INVENTOR(S) : Xu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this
Twenty-eighth Day of May, 2013

Teresa Stanek Rea
*Acting Director of the United States Patent and Trademark Office*